(12) United States Patent
Bulatov et al.

(10) Patent No.: US 11,663,757 B2
(45) Date of Patent: May 30, 2023

(54) SYSTEMS AND METHODS FOR MONITORED TOMOGRAPHIC RECONSTRUCTION

(71) Applicant: Smart Engines Service, LLC, Moscow (RU)

(72) Inventors: Konstantin Bulatovich Bulatov, Moscow (RU); Marina Valerievna Chukalina, Moscow (RU); Alexey Vladimirovich Buzmakov, Moscow (RU); Dmitry Petrovich Nikolaev, Moscow (RU); Vladimir Viktorovich Arlazarov, Moscow (RU)

(73) Assignee: Smart Engines Service, LLC, Moscow (RU)

( * ) Notice: Subject to any disclaimer, the term of this patent is extended or adjusted under 35 U.S.C. 154(b) by 220 days.

(21) Appl. No.: 17/180,397

(22) Filed: Feb. 19, 2021

(65) Prior Publication Data

US 2022/0020185 A1 Jan. 20, 2022

(30) Foreign Application Priority Data

Jul. 15, 2020 (RU) .................. 2020123432

(51) Int. Cl.
*G06T 11/00* (2006.01)
*A61B 6/00* (2006.01)
(52) U.S. Cl.
CPC ............ *G06T 11/006* (2013.01); *A61B 6/42* (2013.01); *A61B 6/542* (2013.01); *G06T 11/008* (2013.01); *G06T 2211/421* (2013.01); *G06T 2211/424* (2013.01)
(58) Field of Classification Search
CPC ................ G06T 11/006; G06T 11/008; G06T 2211/421; G06T 2211/424; A61B 6/42; A61B 6/542; A61B 6/032; A61B 6/5205
See application file for complete search history.

(56) References Cited

U.S. PATENT DOCUMENTS

2019/0122400 A1* 4/2019 Li .................... G06T 7/0012

OTHER PUBLICATIONS

H. Wang, Y. Zhou, S. Su, Z. Hu, J. Liao, and Y. Chang, "Adaptive volterra filter for parallel MRI reconstruction," Eurasip J. Adv Signal Process., vol. 2019, No. 1, Dec. 2019, Art. No. 34, doi: 10.1186/s13634-019-0633-5.

(Continued)

*Primary Examiner* — Courtney D Thomas
(74) *Attorney, Agent, or Firm* — Procopio, Cory, Hargreaves & Savitch LLP

(57) ABSTRACT

A system for monitored tomographic reconstruction, comprising: an x-ray generator configure to generate x-ray beams for scanning an object; detectors configured to capture a plurality of projections for each scan; at least one hardware processor; and one or more software modules that, when executed by the at least one hardware processor, receive the plurality of projections from the detectors and as each of the plurality of projections is received, generate a partial reconstruction, and make a stopping decision with respect to whether or not another projection should be obtained based on a stopping problem and that defines when a reconstructed image quality is sufficient with respect to the expended cost as determined by a stopping rule.

14 Claims, 11 Drawing Sheets

(56) References Cited

OTHER PUBLICATIONS

A.S. Ingacheva and M. V. Chukalina, "Polychromatic CT Data Improvement with One-Parameter Power Correction," Math. Problems in Eng., 2019, Art. ID 1405365, DOI: 10.1155/2019/1405365.

B. A. Berezovskij and A. V. Gnedin, "Theory of choice and the problem of optimal stopping at the best entity." Autom. Remote Control, vol. 42, pp. 1221-1225, 1981.

Y. S. Chow and H. Robbins, "A Martingale System Theorem and Applications," in Proc 4th Berkeley Symp Math Stat Probabilit, vol. 1 Berkeley, Calif.: Univ. of Calif. Press, 1961, pp. 93-104.

A. V. Buzmakov, V. E. Asadchikov, D. A. Zolotov, B. S. Roshchin, Y. M. Dymshits, V. A. Shishkov, M. V. Chukalina, A. S. Ingacheva, D. E. Ichalova, Y. S. Krivonosov, I. G. Dyachkova, M. Balzer, M. Castele, S. Chilingaryan, and A. Kopmann, "Laboratory Microtomographs: Design and Data Processing Algorithms," Crystallography Reports, vol. 63, No. 6, pp. 1057-1061, 2018, DOI: 10.1134/S106377451806007X.

S. van der Walt, J. L. Schonberger, J. Nunez-Iglesias, F. Boulogne, J. D. Warner, N. Yager, E. Gouillart, T. Yu, and the scikit-image contributors, "scikit-image: image processing in Python," PeerJ, vol. 2:e453, 2014, DOI: 10.7717/peerj.453.

E. I. Fokin, S. V. Savel'ev, V. I. Gulimova, E. V. Asadchikov, R. A. Senin, and A. V. Buzmakov, "The morphogenesis and spatial organization of human pineal gland concretions in Alzheimer's disease, schizophrenia, and alcoholism," Archive of pathology, vol. 68, No. 5, pp. 20-22, 2006, (In Russian).

V. Gulimova, A. Proshchina, A. Kharlamova, Y. Krivova, V. Barabanov, R. Berdiev, V. Asadchikov, A. Buzmakov, D. Zolotov, and S. Saveliev, "Reptiles in Space Missions: Results and Perspectives," Int. J. of Molecular Sci., vol. 20, No. 12, 2019, Art. ID 3019, DOI: 10.3390/ijms20123019.

Y. Krivonosov, M. Chukalina, A. Buzmakov, V. Asadchikov, A. Rusakov, A. Mariyanats, V. Popov, I. Zanin, and V. Kulik, "Study of polylactide matrices using x-ray microtomography," Industrial laboratory, Diagnostics of materials, vol. 86, No. 1, pp. 26-31, 2020, DOI: 10.26896/1028-6861-2020-86-1-26-31 (In Russian).

C.-J. Tan, C.-X. Tang, W.-H. Huang, Q.-X. Jin, Y.-C. Du, Q. Luo, P.-D. Wu, D.-H. Liu, L.-M. Zhang, and C. Xu, "Beam and image experiment of beam deflection electron gun for distributed X-ray sources," Nuclear Sci. and Techniques, vol. 30, No. 3, 2019, Art. ID 50, DOI: 10.1007/s41365-019-0561-y.

M. Khoury, H. Li, P. Li, Y. C. Chow, B. Bonef, H. Zhang, M. S. Wong, S. Pinna, J. Song, J. Choi, J. S. Speck, S. Nakamura, and S. P. DenBaars, "Polarized monolithic white semipolar (20-21) InGaN lightemitting diodes grown on high quality (20-21) GaN/sapphire templates and its application to visible light communication," Nano Energy, vol. 67, 2020, Art. ID 104236, DOI: 10.1016/j.nanoen.2019. 104236.

N. Smelkina, A. Kolsanov, S. Chaplygin, P. Zelter, and A. Khramov, "Pulmonary Emphysema Recognition by CT scan," Computer Optics, vol. 41, No. 5, 2017, DOI: 10.18287/2412-6179-2017-41-5-726-731 (In Russian).

M. F. McNitt-Gray, "AAPM/RSNA Physics Tutorial for Residents: Topics in CT," RadioGraphics, vol. 22, No. 6, pp. 1541-1553, 2002, DOI: 10.1148/rg.226025128.

M. C. Horsch and D. Poole, "An anytime algorithm for decision making under uncertainty," in Proc. of the 14th Conf. on Uncertainty in Artificial Intelligence, ser. UAI'98. San Francisco, CA, USA: Morgan Kaufmann Publishers Inc., 1998, pp. 246-255.

A. C. Kak and M. Slaney, Principles of Computerized Tomographic Imaging, ser. Classics in Applied Mathematics. Society for Industrial and Applied Mathematics, Philadelphia, USA, 2001, DOI: 10.1137/1.9780898719277.

T. Buzug, Computed Tomography. Springer-Verlag, Berlin, Heidelberg, 2008, DOI: 10.1007/978-3-540-39408-2.

E. Topal, Z. Liao, M. Löffler, J. Gluch, J. Zhang, X. Feng, and E. Zschech, "Multi-scale X-ray tomography and machine learning algorithms to study MoNi4 electrocatalysts anchored on MoO2 cuboids aligned on Ni foam," BMC Materials, No. 2, 2020, Art. ID 5, DOI: 10.1186/s42833-020-00011-0.

M. Polikarpov, G. Bourenkov, I. Snigireva, A. Snigirev, S. Zimmermann, K. Csanko, S. Brockhauser, and T. R. Schneider, "Visualization of protein crystals by high-energy phase-contrast X-ray imaging," Acta Crystallographica Section D, vol. 75, No. 11, pp. 947-958, 2019, DOI: 10.1107/S2059798319011379.

M. Sokac, I. Budak, M. Katie, Z. Jakovljevic, Z. Santosi, and D. Vukelic, "Improved surface extraction of multi-material components for singlesource industrial X-ray computed tomography," Measurement, vol. 153, 2020, Art. ID 107438, DOI: 10.1016/j.measurement.2019.107438.

P. Hermanek, F. Zanini, and S. Carmignato, "Traceable Porosity Measurements in Industrial Components Using X-Ray Computed Tomography," J. of Manufacturing Sci. and Eng., vol. 141, No. 5, 2019, Art. ID 051004, DOI: 10.1115/1.4043192.

A. B. Watson, Q. J. Hu, and J. F. McGowan, "Digital video quality metric based on human vision," J. Electron. Imag., vol. 10, No. 1, pp. 2030, 2001, doi: 10.1117/1.1329896.

K. J. Batenburg, S. Bals, J. Sijbers, C. Kübel, P. A. Midgley, J. C. Hernandez, U. Kaiser, E. R. Encina, E. A. Coronado, and G. V. Tendeloo, "3D imaging of nanomaterials by discrete tomography," Ultramicroscopy, vol. 109, No. 6, pp. 730-740, 2009, DOI: 10.1016/j.ultramic.2009.01.009.

A. Pakhnevich, A. Kurkin, A. Lavrov, K. Tarasenko, E. Kovalenko, A. Kaloyan, and K. Podurets, "Synchrotron and Neutron Tomography of Paleontological Objects on the Facilities of the Kurchatov Institute," J. of Imaging, vol. 4, No. 8, 2018, Art. ID 103, DOI: 10.3390/jimaging4080103.

I. Bukreeva, A. Mittone, A. Bravin, G. Festa, M. Alessandrelli, P. Coan, V. Formoso, R. G. Agostino, M. Giocondo, F. Ciuchi, M. Fratini, L. Massimi, A. Lamarra, C. Andreani, R. Bartolino, G. Gigli, G. Ranocchia, and A. Cedola, "Virtual unrolling and deciphering of Herculaneum papyri by X-ray phase-contrast tomography," Sci. Reports, vol. 6, 2016, Art. ID 27227, DOI: 10.1038/srep27227.

X. Duan, J. Cheng, L. Zhang, Y. Xing, Z. Chen, and Z. Zhao, "X-ray cargo container inspection system with few-view projection imaging," Nuclear Instruments and Methods in Phys. Res. Section A, vol. 598, No. 2, pp. 439-444, 2009, DOI: 10.1016/j.nima.2008.08.151.

N. Hättenschwiler, S. Merks, and A. Schwaninger, "Airport security x-ray screening of hold baggage: 2d versus 3d imaging and evaluation of an onscreen alarm resolution protocol," in Int. Carnahan Conf. on Security Tech. (ICCST), 2018, pp. 1-5, DOI: 10.1109/CCST.2018.8585713.

B. Wildman-Tobriner, B. C. Allen, and C. M. Maxfield, "Common Resident Errors When Interpreting Computed Tomography of the Abdomen and Pelvis: A Review of Types, Pitfalls, and Strategies for Improvement," Current Problems in Diagnostic Radiology, vol. 48, No. 1, pp. 4-9, 2019, DOI: 10.1067/j.cpradiol.2017.12.010.

Y. Kwong, A. O. Mel, G. Wheeler, and J. M. Troupis, "Four-dimensional computed tomography (4DCT): A review of the current status and applications," J. of Medical Imaging and Radiation Oncology, vol. 59, No. 5, pp. 545-554, 2015, DOI: 10.1111/1754-9485.12326.

C.-H. Chien, F.-C. Shih, C.-Y. Chen, C.-H. Chen, W.-L. Wu, and C.-W. Mak, "Unenhanced multidetector computed tomography findings in acute central pulmonary embolism," BMC Medical Imaging, vol. 19, 2019, Art. ID 65, DOI: 10.1186/s12880-019-0364-y.

J. Wu, F. Qi, and G. Shi, "Image quality assessment based on improved structural similarity," in Advances in Multimedia Information ProcessingPCM. Berlin, Germany: Springer, 2012, pp. 153163, doi: 10.1007/978-3-642-34778-8_14.

K.-J. Yoo, D. Choi, B. W. Choi, S.-H. Lim, and B.-C. Chang, "The comparison of the graft patency after coronary artery bypass grafting using coronary angiography and multi-slice computed tomography," Europ. J. of Cardio-Thoracic Surgery, vol. 24, No. 1, pp. 86-91, 2003, DOI: 10.1016/31010-7940(03)00192-1.

D. R. Coles, M. A. Smail, I. S. Negus, P.Wilde, M. Oberhoff, K. R. Karsch, and A. Baumbach, "Comparison of Radiation Doses From Multislice Computed Tomography Coronary Angiography and Conventional Diagnostic Angiography," J. of the American College of Cardiology, vol. 47, No. 9, pp. 1840-1845, 2006, DOI: 10.1016/j.iacc.2005.11.078.

(56) References Cited

OTHER PUBLICATIONS

I. Kuchin, T. Imaev, P. Lepilin, A. Kolegaev, I. Medvedeva, A. Komlev, S. Ternovoi, and R. Akchurin, "State of the art of the problem concerning endovascular treatment of abdominal aortic aneurysms of intrarenal localization," Angiol Sosud Khir, vol. 24, No. 3, pp. 60-65, 2018, (In Russian).
A. E. Hughes, A. Trinchi, F. F. Chen, Y. S. Yang, I. S. Cole, S. Sellaiyan, J. Carr, P. D. Lee, G. E. Thompson, and T. Q. Xiao, "The application of multiscale quasi 4D CT to the study of SrCrO4 distributions and the development of porous networks in epoxy-based primer coatings," Progress in Organic Coatings, vol. 77, No. 11, pp. 1946-1956, 2014, DOI: 10.1016/j.porgcoat.2014.07.001.
T. Suzuki, T. Shiotani, and M. Ohtsu, "Evaluation of cracking damage in freeze-thawed concrete using acoustic emission and X-ray CT image," Construction and Building Materials, vol. 136, pp. 619-626, 2017, DOI: 10.1016/j.conbuildmat.2016.09.013.
Y. Wang, R. Song, J.-J. Liu, M.-M. Cui, and P. G. Ranjith, "Pore scale investigation on scaling-up micro-macro capillary number and wettability on trapping and mobilization of residual fluid," J. of Contaminant Hydrology, vol. 225, 2019, Art. ID 103499, DOI: 10.1016/j.jconhyd.2019.103499.
T. dos Santos Rolo, A. Ershov, T. van de Kamp, and T. Baumbach, "In vivo X-ray cine-tomography for tracking morphological dynamics," Proc. of the National Academy of Sci., vol. 111, No. 11, pp. 3921-3926, 2014, DOI: 10.1073/pnas. 1308650111.
S. E. Adamczak, F. J. Bova, and D. J. Hoh, "Intraoperative 3D Computed Tomography: Spine Surgery," Neurosurgery Clinics of North America, vol. 28, No. 4, pp. 585-594, 2017, DOI: 10.1016/j.nec.2017.06.002.
H. Villarraga-Gómez, C. Peitsch, A. Ramsey, and S. Smith, "The Role of Computed Tomography in Additive Manufacturing," in ASPE and euspen Summer Topical Meeting: Advancing Precision in Additive Manufacturing, 2018, pp. 201-210.
J. Z. Liang, P. J. La Riviere, G. El Fakhri, S. J. Glick, and J. Siewerdsen, "Guest Editorial Low-Dose CT: What Has Been Done, and What Challenges Remain?" IEEE Trans. on Med. Imag., vol. 36, No. 12, pp. 2409-2416, 2017, DOI: 10.1109/TML2017.2768978.
M. K. Kalra, M. M. Maher, T. L. Toth, L. M. Hamberg, M. A. Blake, J.-A. Shepard, and S. Saini, "Strategies for CT Radiation Dose Optimization," Radiology, vol. 230, No. 3, pp. 619-628, 2004, DOI: 10.1148/radiol.2303021726.
T. L. Slovis, "The ALARA Concept in Pediatric CT: Myth or Reality?" Radiology, vol. 223, No. 1, pp. 5-6, 2002, DOI: 10.1148/radiol.2231012100.
A. Sabarudin and Z. Sun, "Radiation dose measurements in coronary CT angiography," World J. of Cardiology, vol. 5, No. 12, pp. 459-464, 2013, DOI: 10.4330/wjc.v5.i12.459.
L. W. Goldman, "Principles of CT: Radiation Dose and Image Quality," J. of Nuclear Medicine Tech., vol. 35, No. 4, pp. 213-225, 2007, DOI: 10.2967/jnmt.106.037846.
N. Irnstorfer, E. Unger, A. Hojreh, and P. Homolka, "An anthropomorphic phantom representing a prematurely born neonate for digital x-ray imaging using 3D printing: Proof of concept and comparison of image quality from different systems," Sci. Reports, vol. 9, No. 1, 2019, Art. ID 14357, DOI: 10.1038/s41598-019-50925-3.
K. MacGregor, I. Li, T. Dowdell, and B. G. Gray, "Identifying Institutional Diagnostic Reference Levels for CT with Radiation Dose Index Monitoring Software," Radiology, vol. 276, No. 2, pp. 507-517, 2015, DOI: 10.1148/radiol.2015141520.
G. Wang, H. Yu, and Y. Ye, "A scheme for multisource interior tomography," Med. Phys., vol. 36, No. 8, pp. 3575-3581, 2009, DOI: 10.1118/1.3157103.
T. K. Mittal and M. B. Rubens, Computed Tomography Techniques and Principles. Part a. Electron Beam Computed Tomography. London: Springer London, 2006, pp. 93-98, DOI: 10.1007/1-84628-156-3_6.
W. Yang, H. Zhang, J. Yang, J. Wu, X. Yin, Y. Chen, H. Shu, L. Luo, G. Coatrieux, Z. Gui, and Q. Feng, "Improving Low-Dose CT Image Using Residual Convolutional Network," IEEE Access, vol. 5, pp. 24 698-24 705, 2017, DOI: 10.1109/ACCESS.2017.2766438.
Z. Wang, A. C. Bovik, H. R. Sheikh, and E. P. Simoncelli, "Image quality assessment: From error visibility to structural similarity," IEEE Trans. Image Process., vol. 13, No. 4, pp. 600612, Apr. 2004, doi: 10.1109/tip.2003.819861.
K. Bulatov, N. Razumnyi, and V. V. Arlazarov, "On optimal stopping strategies for text recognition in a video stream as an application of a monotone sequential decision model," Int. J. on Document Analysis and Recognit., vol. 22, No. 3, pp. 303-314, 2019, DOI: 10.1007/s10032-019-00333-0.
K. Bulatov, B. Savelyev, and V. V. Arlazarov, "Next integrated result modelling for stopping the text field recognition process in a video using a result model with per-character alternatives," in 12th Int. Conf. on Machine Vision (ICMV, vol. 11433. SPIE, 2020, pp. 710-716, DOI: 10.1117/12.2559447.
T. Chernov, N. Razumnuy, A. Kozharinov, D. Nikolaev, and V. Arlazarov, "Image quality assessment for video stream recognition systems," J. of Informat. Tech. and Comput. Sys., vol. 4, pp. 71-82, 2017, (In Russian).
S. Zilberstein, "Using anytime algorithms in intelligent systems," AI Magazine, vol. 17, No. 3, pp. 73-83, 1996, DOI: 10.1609/aimag.v17i3.1232.
T. Ferguson, Mathematical statistics: a decision theoretic approach, ser. Probability and mathematical statistics. Academic Press, 1967.
T. S. Ferguson, "Optimal stopping and applications," 2008. [Online]. Available: {https://www.math.ucla.edu/~tom/Stopping}.
S. Basu and Y. Bresler, "O(N2 log2 N) filtered backprojection reconstruction algorithm for tomography," IEEE Trans. on Image Process., vol. 9, No. 10, pp. 1760-1773, 2000, DOI: 10.1109/83.869187.
M. Beister, D. Kolditz, and W. A. Kalender, "Iterative reconstruction methods in X-ray CT," Physica Medica, vol. 28, No. 2, pp. 94-108, 2012, DOI: 10.1016/j.ejmp.2012.01.003.
K. Bulatov, M. Chukalina, and D. Nikolaev, "Fast X-Ray Sum Calculation Algorithm for Computed Tomography Problem," Bull. of the South Ural State Univ. Ser. Math. Modelling, Programming & Comp. Software, vol. 13, No. 1, pp. 95-106, 2020, DOI: 10.14529/mmp200107.
E. A. Cheremukhin and A. I. Chulichkov, "On the application of computer measurement systems in tomography," Comput. Math. and Math. Phys., vol. 45, No. 4, pp. 716-726, 2005, (In Russian).

\* cited by examiner

SYSTEMS AND METHODS FOR MONITORED TOMOGRAPHIC RECONSTRUCTION

CROSS-REFERENCE TO RELATED APPLICATIONS

This application claims priority to Russian Patent App. No. 2020123432, filed on Jul. 15, 2020, which is hereby incorporated herein by reference as if set forth in full.

BACKGROUND

1. Technical Field

The embodiments described herein are related to computed tomography, and more particularly to monitored reconstruction techniques that achieve higher mean reconstruction quality for a given average number of projections.

2. Related Art

Computed tomography (CT) is a powerful non-destructive technique for constructing detailed images of internal object areas. Computed tomography has important applications in such fields as industry, physics, chemistry, biology, medicine, and others. Analysis of a three-dimensional internal structure of objects is required for the study of multi-material components, for characterization of object's properties, or to analyze nanostructures. More problem-specific applications include archaeology, where computed tomography is used for the analysis of precious artifacts, or to read historical manuscripts that cannot be manually handled. Increased international trade requires automatization of cargo inspection, which could be performed using tomographic analysis, and there are studies of CT application for airport luggage inspection systems. Medical CT scanning is widely used to diagnose muscle and bone disorders, to pinpoint the location of tumors, and to monitor the effectiveness of certain treatments.

In conventional tomography, the target object is probed with X-rays at different angles. The tomographic projections are collected relying on the property of X-ray attenuation as the projections traverse the matter. Attenuation is the reduction of the intensity of an X-ray beam, used to create an image. The attenuation may be caused by absorption or by deflection (scattering) of photons from the beam and can be affected by beam energy and the atomic number of the absorber.

Active studies continue to improve both the technical side and the diagnostic side of medical CT applications. Along with the development of techniques and protocols for the study of stationary objects, another actively developed application is the study of dynamic objects, or the so-called 4D-tomography. 4D reconstruction techniques in a medical field allow studying organs that are in continuous motion, such as lungs and heart.

Industrial applications of 4D tomography include monitoring of the development of porous networks, cracking damage, local fluid flow, and more. An important issue for conventional CT applications is the time required to obtain X-ray projections and to perform the image reconstruction. It is particularly relevant in the medical field, both for diagnostic purposes and for more advanced applications such as guiding surgical operations. Reconstruction speed requirement is also present in the industry, for such applications as quality control on assembly lines.

Another important issue for conventional computed tomography is radiation exposure, since only a small class of studied objects has radiation resistance. The decrease of imparted dose during tomographic scanning is of great importance, particularly in the medical field. Different applications of computed tomography grouped by the time and radiation exposure requirements are presented in FIG. 1.

As can be seen, applications like 3D analysis in science/industry: inspection of composition and morphological structure for archaeology, material science, geophysics, etc.; 4D analysis in science/industry: development of porous networks, cracking damage, local fluid flow, etc.; and applications such as assembly quality control, travel security scanners, cargo handling and logistics, etc., have relatively fewer dose and time restrictions, while application like 3D analysis in medicine: brain, spine, soft tissues, dentistry, etc.; and 4D analysis in medicine: heart, lungs, blood vessels, etc., have relative more dose and time restrictions.

The amount of X-ray radiation that is absorbed during the imaging process contributes to the object's radiation dose. In spite of there being an understood need to reduce the absorbed radiation dose, within an ALARA concept (As Low as Reasonably Achievable), there is no consensus regarding how the dose should be expressed and measured.

Multiple approaches can be used to describe the CT-delivered dose, the most relevant being absorbed dose, effective dose, background equivalent radiation time, and CT dose index (CTDI). The absorbed dose is the energy absorbed per unit of mass and it is measured in grays (Gy). The unit of measurement for the whole-body radiation dose (called the "effective dose") is the millisievert (mSv). Medical doctors use the "effective dose" when they talk about the risk of radiation exposure of the entire body, as it takes into account how sensitive different tissues are to the radiation.

The effective dose allows a rough comparison of different CT scenarios and scanning techniques, but it provides only an approximate estimate of the true risk. For more precise risk estimation, the organ dose is the preferred measurement. Organ doses can be calculated or measured using anthropomorphic phantoms. In anthropomorphic phantoms ALARA can be considered on a local level to be met using the lowest possible exposure with the available equipment and software while maintaining diagnostic interpretability.

The radiation dose depends on a large number of factors. The most important are the number of projection angles, the X-ray tube current and voltage, the size of the object, the axial scan range, the scan pitch (the degree of overlap between adjacent CT slices), scanning time and the specific design of the tomograph. Requirements for newer generations of tomography scanners are defined by advanced measurement protocols that prevent reproductive and apoptotic death of cells after radiation injury.

Along with the optimization of set-ups based on the use of a gantry, conventional scanners are created with a controlled collection of projections with an arbitrary angle. This is implemented in two main ways: either X-ray beams are registered by multiple source-detector pairs for data acquisition or the X-ray source-point is swept electronically. It is always the case that the relative noise in CT images will increase as the radiation dose decreases, which means that there will always be a trade-off between the need for low-noise images and the desire to achieve low doses of radiation. If the tube current and voltage are fixed, it is possible to decrease the radiation dose by decreasing the exposure time or decreasing the number of projection angles.

Overall, optimized protocols and procedures have been introduced, based both on the new generation of tomographic scanners and on adaptive iterative reconstruction software, in an effort to reduce the mean imparted dose; however, the quality of the reconstructed images given the same protocol can, and possible should be different for different objects. And if all objects (e.g. all medical patients) are scanned using the same protocol, then some will absorb an optimal radiation dose (that is, in relation to the required reconstruction quality), some—in excess, and some will get a dose that is insufficient to produce an acceptable reconstruction and will have to be subjected to a re-scan with a modified setting.

SUMMARY

Systems and methods for monitored reconstruction, constructing stopping rules for various reconstruction quality metrics and the experimental evaluation thereof are described herein. Due to stopping at different times for different objects, the systems and methods described herein achieve a higher mean reconstruction quality for a given mean number of X-ray projections. Conversely, fewer projections on average are used to achieve the same mean reconstruction quality.

According to one aspect, a system for monitored tomographic reconstruction, comprising: an x-ray generator configure to generate x-ray beams for scanning an object; detectors configured to capture a plurality of projections for each scan; at least one hardware processor; and one or more software modules that, when executed by the at least one hardware processor, receive the plurality of projections from the detectors and as each of the plurality of projections is received, generate a partial reconstruction, and make a stopping decision with respect to whether or not another projection should be obtained based on a stopping problem and that defines when a reconstructed image quality is sufficient with respect to the expended cost as determined by a stopping rule.

These and other features, aspects, and embodiments are described below in the section entitled "Detailed Description."

BRIEF DESCRIPTION OF THE DRAWINGS

Features, aspects, and embodiments are described in conjunction with the attached drawings, in which.

DETAILED DESCRIPTION

Figure 1:
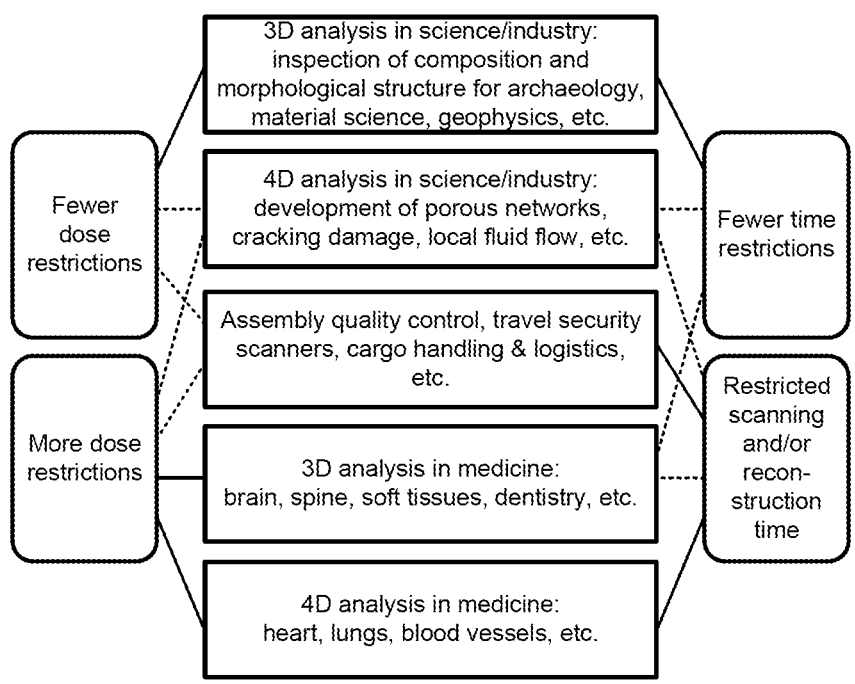
FIG. 1 is a diagram illustrating Computed tomography applications in reference to the restrictions on time and radiation dose.

In an embodiment, systems, methods, and non-transitory computer-readable media are disclosed for a CT scanning procedure as an anytime algorithm. Anytime algorithms as a way of thinking about algorithms with quantifiable goals are useful when the cost of computation (whether in terms of time or other quantities) is comparable, or at least relevant, in relation to the cost of error. Intelligent systems such as decision support systems and computer vision systems use the model of anytime algorithms to represent and manage the trade-off between the quality of the result and the time required to obtain it. If the tomographic procedure is not broken down into separate stages scanning and reconstruction, the tomographic scanning cost can be either expressed in terms of time required to collect the projections, or in terms of radiation dose delivered to the object. If the reconstruction process is monitored during the process of obtaining projections, the decision to stop the scanning process may be made when the sufficient reconstructed image quality is achieved. We call this approach a monitored reconstruction.

The embodiments described herein can be configured to build a model of the monitored reconstruction process and evaluate its feasibility, advantages, and disadvantages.

I. FRAMEWORK

One of the most important properties of anytime algorithms is monotonicity, which requires the quality of the result to be a non-decreasing function of time (computational cost) and input quality. Putting aside the input quality, if partial reconstruction in the tomographic imaging process is considered, each based on a limited number of currently acquired projections, it is natural to expect the reconstruction results to "improve" over time. Thus, such imaging process can be considered an anytime algorithm. Such a process can be considered as a monitored reconstruction process. In this section, a model of such a process in accordance with at least one example embodiments is described and its properties analyzed.

A. Projections and Partial Reconstruction

Assuming the physical properties of the tomography setup are fixed, including the protocol for acquiring projections, dimensions, resolution, etc., then given a fixed experimental setup consider a sequential tomographic imaging process of an object $\theta \in \Theta$ (the imaging target) can be considered. During the process, we observe a sequence of projections $X=(X_1; X_2; \ldots)$ according to a fixed experimental protocol. Each $X_i$ can be viewed as a random vector dependent on $\theta$, which has a sample space $\chi$ and encodes both the projection and the angle with which this projection is acquired.

Given a sequence of projections $(x_1; x_2; \ldots; x_n) \in \chi_n$ tomographic reconstruction can be performed, thus obtaining a reconstruction result $R_n(x_1; x_2; \ldots; x_n)$. For the purposes of the constructed anytime algorithm model we will assume that the reconstruction $R_n(x_1; \ldots; x_n)$ is performed after each projection $X_n=x_n$ is acquired. The final goal is to obtain a reconstruction result with the lowest value of the reconstruction error $\varepsilon(R_n(x_1, \ldots, x_n), \theta)$, which is defined for any object $\theta \in \Theta$ and all possible reconstruction results. In terms of anytime algorithms by defining an error function e it is stated that the algorithm has the property of measurable quality; however, this does not necessarily mean that it has recognizable quality—the precise value of the current reconstruction error $\varepsilon(R_n(x_1, \ldots, x_n), \theta)$ might not be possible to determine at run time. The assumed property of monotonicity implies that the value of $\varepsilon(R_n(x_1, \ldots, x_n), \theta)$ decreases over time (that is, as n increases).

Considering the differences in the quality of partial reconstructions implies that the acquired projections also have a cost. The need to balance the error of the currently available reconstruction result and the cost of obtaining it brings forward the problem of optimal stopping—determining the moment when the acquisition of projections should stop and the current reconstruction result should be considered final.

It is important that if given a fixed error function $\varepsilon$ and a fixed experimental setup the speed of the error value $\varepsilon(R_n(x_1, \ldots, x_n), \theta)$ has the same decrease speed for all $\theta \in \Theta$, then the stopping rules are not required at all—the number of projections required to reach a certain level of error would be the same. Thus, to even consider stopping rules that would allow stopping at different process stages, depending on the collected projections and tomographical reconstruction results, the following hypothesis is needed:

Hypothesis 1 (H1) The decrease speed of the error value $\varepsilon(R_n(x_1, \ldots, x_n), \theta)$ depends on the object $\theta$.

B. Projection Cost and Stopping Rules

To reflect the cost of acquired projections, whether in terms of time or dosage, and the cost of computation required to perform partial reconstructions, a sequence of real-valued cost functions can be defined: $c=(c_0, c_1(x_1), c_2(x_1, x_2), \ldots)$. Each cost function $c_n$ has a domain $\chi^n$ and denotes the total cost of acquiring projections $X_1=x_1, \ldots, X_n=x_n$ and obtaining a reconstruction result $R_n(x_1, \ldots, x_n)$, relative to the cost of the reconstruction error. It can be assumed that the cost of taking no observations at all is zero (i.e. $c_0=0$), taking additional observations always costs a non-negative amount, i.e. $c_n(x_1, \ldots, x_n) < c_{n+1}(x_1, \ldots, x_n, x_{n+1})$, and the cost does not converge to any finite limit, i.e. $c_n(x_1, \ldots, x_n) \to \infty$ with $n \to \infty$. The total loss $L_n(x_1, \ldots, x_n)$ of acquiring n projections and taking $R_n(x_1, \ldots, x_n)$ as the final reconstruction result is a sum of the reconstruction error and the cost of obtained observations:

$$L_n(x_1, \ldots, x_n) = \varepsilon(R_n(x_1, \ldots, x_n), \theta) + c_n(x_1, \ldots, x_n). \quad (1)$$

A stopping rule is defined as a sequence of functions $\varphi=(\varphi_0, \varphi_1(x_1), \varphi_2(x_1, x_2), \ldots)$ with $\varphi_n$ having a domain $\chi^n$ and $0 \leq \varphi_n(x_1, \ldots, x_n) \leq 1$ for all n. The value of $\varphi_n(x_1, \ldots, x_n)$ represents the conditional probability of stopping given that n projections has been acquired and $X_1=x_1, \ldots, X_n=x_n$. The value $\varphi_0$ is constant and represents the probability of acquiring no projections. With a given stopping rule $\varphi$ a random variable N can be defined, which represents the random stopping time. Stopping rule $\varphi$ and random stopping time N are related as follows:

$$\varphi_n(x_1, \ldots, x_n) = P(N=n|N \geq n, X_1=x_1, \ldots, X_n=x_n). \quad (2)$$

The probability mass function of N given the obtained observations $X_1=x_1, X_2=x_2, \ldots$ is denoted as $\psi=(\psi_0, \psi_1(x_1), \ldots, \psi_\infty(x_1, x_2, \ldots))$, where $$\psi_n(x_1, \ldots, x_n) = P(N=n|X_1=x_1, \ldots, X_n=x_n), \psi_\infty(x_1, x_2, \ldots) = P(N=\infty|X_1=x_1, X_2=x_2, \ldots) \quad (3)$$

The stopping time probability mass functions $\psi$ are related to the stopping rule $\varphi$ as follows:

$$\psi_0 = \phi_0, \quad (4)$$

$$\psi_n(x_1, \ldots, x_n) = \phi_n(x_1, \ldots, x_n) \prod_{i=0}^{n-1}(1 - \phi_i(x_1, \ldots, x_i)),$$

$$\psi_\infty(x_1, x_2, \ldots) = 1 - \sum_{n=0}^{\infty} \psi_n(x_1, \ldots, x_n).$$

The stopping problem involves choosing a stopping rule $\varphi$ which would minimize the expected loss $V(\varphi)$, which can be expressed as follows:

$$V(\phi) = E\left(\sum_{n=0}^{=\infty} \psi_n(X_1, \ldots, X_n) L_n(X_1, \ldots, X_n)\right), \quad (5)$$

where the "$=\infty$" indicates the summation over values of n from 0 to $\infty$, including $\infty$. In terms of the random stopping time N the expected loss can be expressed as follows:

$$V(\varphi) = E(L_N(X_1, \ldots, X_N)). \quad (6)$$

The stopping problem of the monitored tomographic reconstruction entails the minimization of the expected loss (6) across all possible stopping rules. The solution to the stopping problem (6) defines the time when the monitored reconstruction process should be stopped, i.e. when the reconstructed image quality is sufficient with respect to the expended cost.

The introduction of stopping rules concludes the full model of the monitored tomographic reconstruction process. The scheme of the constructed model is presented in FIG. 2. As can be seen, a projection $x_1$ is received at block 202, an example of which (204) is shown. The partial reconstruction $R_i$ then takes place at black 206. Example partial reconstructions (208) are shown. The stopping decision is then made, e.g., by solving the problem of minimization of expected loss (6) in block 210 and the process is then stopped, or not at block 212.

For the sake of clarity in the subsequent sections $L_n$, $R_n$, $c_n$ are treated as synonyms of $L_n(x_1, \ldots, x_n)$, $R_n(x_1, \ldots, x_n)$, and $c_n(x_1, \ldots, x_n)$ respectively.

C. From Anytime to any Dose

By incorporating the time required to acquire the projections $x_1, \ldots, x_n$ and the time required to produce a reconstruction $R_n$ using some fixed reconstruction algorithm into the cost functions $c_n$ a model of the tomographic imaging process can be obtained as an anytime algorithm in its general sense. By solving the stopping problem the required level of the reconstruction error (in terms of the function $\varepsilon$) can be reached in the shortest time on average, and, conversely, obtain on average the lowest reconstruction error given the same measurement time.

Within the scope of anytime algorithms, the cost functions $c_n$ are mostly associated with measurement time, which in this case includes the time required to collect the projections and to reconstruct the image. If an integral reconstruction technique, such as FBP (Filtered Back Projection), is used, then the reconstruction time and projection collection time could be considered commensurable, and the monitored reconstruction process with FBP may be regarded as an anytime algorithm, capable of delivering improved reconstruction results over time, and with the ability of stopping the process when the result becomes satisfactory.

Integral reconstruction techniques produce poor reconstruction results if only a small amount of projections is available, or if the projections have low contrast and poor signal-to-noise ratio. Algebraic techniques have an advantage in this regard, but they have a significantly higher computational complexity. Algebraic methods are iterative and the computational time for a single iteration is comparable with FBP. Monitored reconstruction process with algebraic methods is possible if the algorithms are modified such that the iterations are resumed from the previous state taking into account the newly acquired projections.

An interesting special case presents itself if the time required to acquire the projections and to perform reconstruction is disregarded, and focus instead on the radiation dose alone. In this case, the process can be viewed as an "any dose" algorithm, where the optimal stopping problems deals with joint optimization of the reconstruction quality and radiation dose required to obtain the algorithm. In the simplest case if each projection imparts a fixed dose c>0 and the exposure between projections is negligible, the cost functions can be defined as follows:

$$c_n(x_1, \ldots, x_n) = n \cdot c. \tag{7}$$

The stopping problem (6) with the observation cost function (7) requires choosing a stopping rule that would allow reaching the desired reconstruction quality with the minimal average number of acquired projections, i.e. the minimal imparted dose.

D. Error Metrics

Given a fixed experimental setup in order to consider the optimal stopping problem (6) we need to define the reconstruction error function $\varepsilon(R_n, \theta)$ for an arbitrary object $\theta$.

Defining the reconstructed image quality is in itself a separate topic of discussion, with a multitude of existing approaches and with many task-oriented variations. Some of the methods of describing the reconstructed image quality include the analysis of its spatial resolution, noise level, or characteristic reconstruction artifacts. Some image quality metrics try to mimic the human perception and either predict the perceived image quality or perceived similarity between two images. This category includes such metrics as SSIM, ISSIM, DVQ, and others. Each of these metrics estimate in one way or another the expressiveness of object features in the image.

How well the partial reconstruction results $R_n$ estimate the "ideal" reconstruction result $R^*(\theta)$ can be analyzed in terms of the absolute and relative estimation errors. Three error functions can be considered, all of them based on an $L_2$ norm in the space of reconstruction results, interpreted as single-channel images with real-valued pixels:

1) RSRE: root square reconstruction error, or an absolute error in terms of the $L_2$ norm:

$$RSRE(R_n, \theta) = \|R_n - R^*(\theta)\|_2; \tag{8}$$

2) NRSRE: a normalized version of RSRE, or a relative error in terms of the $L_2$ norm:

$$NRSRE(R_n, \theta) = \frac{\|R_n - R^*(\theta)\|_2}{\|R^*(\theta)\|_2}; \tag{9}$$

3) S-RSRE: a normalization of RSRE in relation to the sum $S(R^*(\theta))$ of pixel values of the "ideal" image:

$$S\text{-}RSRE(R_n, \theta) = \frac{\|R_n - R^*(\theta)\|_2}{S(R^*(\theta))}. \tag{10}$$

While the comparison of reconstructed images using RSRE error (8) is the most straightforward, employing various normalization might be beneficial for the analysis of the effects of image artifacts and noise. The most natural normalization NRSRE (9) is defined in relation to the $L_2$ of the target image. The downside of this normalization presents itself when the normalization parameter $\|R^*(\theta)\|_2$ needs to be estimated at a given process stage with a limited number of acquired measurements, as the currently obtained projections cannot be used to calculate the $L_2$ norm of the target image, and some prediction algorithms need to be involved (see subsection I-E). For this reason we also consider a second type of normalization (10) based on the Radon invariant—the sum of all pixel values of the reconstructed image. This value corresponds to the sum of signal values in each projection, independent from the angle, barring noise. Thus the value of $S(R^*(\theta))$ can be estimated on any stage of the process using the available projections.

When focusing on the anytime and "anydose" aspects of the imaging process, regardless of how the reconstruction error is defined, it always has two distinct components. The first component is related to the scanning setup, the properties of the object, settings of the emitter and the detector, and the algorithm which is used to reconstruct an image using the collected projections. The second component is related to the number of used projections—the fewer projections that are used, the higher the error value would be. The monitored reconstruction process does not change the factors which influence the first component: the scanning protocol is fixed, as well as the reconstruction algorithm. However, different solutions for the stopping problem (6) will lead to a different number of projections used for different objects.

Consider a partial reconstruction result $R_n$ which was obtained during the monitored tomographic reconstruction process, and which has low quality, i.e. there are artifacts which render the image useless for further analysis, such as medical diagnostics. Does that mean that the process should continue, and more projections should be acquired for the image to improve? Or does that mean that the process should be stopped, and some other experimental parameters need to be changed? To answer these questions, one has to consider not the absolute image quality, but rather how much the image would change if more projections are obtained.

In a traditional tomographical imaging process the number of projections which would be taken before the reconstruction is known in advance. In the monitored reconstruction case, it can also be assumed that the capturing protocol defines a natural stopping point at the stage n T, where all projections are acquired. Thus the last reconstruction result $R_T$ is the one obtainable with all projections scheduled in the experiment. In order to analyze the specific impact of the stopping rules, one goal is to measure the error component which is related to the number of used projections. To achieve that, the last reconstruction result $R_T$ can be regarded, instead of the ground truth for the stopping problem. This would mean that if the error function value reaches zero, the obtained reconstruction result is as good as it can get with a given measurement protocol.

If it is assumed that there is a stage n=T where the process must stop regardless of the obtained result, the problem (6) can be described as a finite horizon stopping problem.

E. Solving the Stopping Problem

For finite horizon stopping problems with known distributions of $X_1, X_2, \ldots$ and known functions $L_n$ (1), the general approach for finding an optimal stopping rule is backwards induction. A special case of the optimal stopping problems are monotone stopping problems, for which the backwards induction approach leads to a formulation of a family of optimal stopping rules denoted as k-stage look-ahead rules.

For brevity, $E_n(\cdot)$ can represent the conditional expectation $E(\cdot | X_1=x_1, \ldots, X_n=x_n)$ of a random variable given that the first n observations are taken. Let $A_n$ denote the event $\{L_n \leq E_n(L_{n+1})\}$. The optimal stopping problem is defined as monotone if $\forall_n \geq 0: A_n \subset A_{n+1}$, in other words, if at some stage n the loss function is not higher than the expected loss at the next stage, then this will be true for all future stages as well. In the terminology of anytime algorithms, the corresponding, though stronger, requirement is one of diminishing returns, which assumes that the improvement in quality is largest at the early stages of the process and diminishes over time.

Using backwards induction it can be proven that for the monotone stopping problems an optimal stopping rule has the following form:

$$N_{1\text{-}sla} = \min\{n \geq 0: L_n \leq E_n(L_{n+1})\}. \tag{11}$$

The rule $N_{1\text{-}sla}$ (11) stops at the earliest stage when the current loss becomes less or equal to the expected loss at the next stage. It is called a "1-stage look-ahead" rule, or a "myopic" rule. With the loss function (1) the myopic rule takes the following form:

$$N_{1\text{-}sa} = \min\{n \geq 0: \varepsilon(R_n, \theta) - E_n(\varepsilon(R_{n+1}, \theta)) \leq E_n(c_n+1) - c_n\}. \tag{12}$$

For the case of monotone stopping problems where the error term of the loss function (1) is expressed as a distance $\rho$ from an obtained result to some "ideal" value, i.e., $\varepsilon(R_n, \theta) = \rho(R_n, R^*(\theta))$, approximation of the myopic rule (11) is proposed. Instead of estimating the difference between the current error and the expected error at the next stage it is proposed to estimate the expected distance between the current result to the result that would be obtained on the next stage. By means of triangle inequality, the left-hand side of the inequality in (12) is bounded by this value. Thus, an alternative stopping rule is obtained:

$$N_\Delta = \min\{n \geq 0: E_n(\rho(R_n, R_{n+1})) \leq E_n(c_{n+1}) - c_n\}. \tag{13}$$

As an approach for solving the optimal stopping problem (6) with an error term in the loss function $L_n$ (1) expressed as an approximation error RSRE (8) of the final re-construction result $R_T$ by the partial reconstruction result $R_n$, let us use a variant of the stopping rule $N_\Delta$ (13) under the following assumption:

Hypothesis 2 (H2) The distances between two consecutive tomographical reconstruction results in terms of the $L_2$ metric decrease over time.

Using triangle inequality it can be shown that under the hypothesis H2 at the stage when the stopping conditions for the rule (13) are satisfied, the stopping problem becomes monotone starting from this stage and it is optimal to stop. The rule (13) then takes the following form:

$$N_\Delta^{RSRE} = \min\{n \geq 0: E_n(\|R_n - R_{n+1}\|_2) \leq E_n(c_{n+1}) - c_n\}. \tag{14}$$

In the cases of NRSRE (9) and S-RSRE (10), the stopping rule (14) can be used under the same hypothesis H2.

However, the expression on the right hand side of the inequality needs to be multiplied by $\|R^*(\theta)\|_2$ and $S(R^*(\theta))$, respectively. Since from the perspective of a stopping rule the best approximation of the ground truth is the reconstruction result $R_T$ on the last stage, the stopping rules for the error functions NRSRE (9) and S-RSRE (10) can be expressed as follows:

$$N_\Delta^{NRSRE} = \min\{n \geq 0: E_n(\|R_n - R_{n+1}\|_2) \leq \|R_T\|_2 \cdot (E_n(c_{n+1}) - c_n)\}, \tag{15}$$

$$N_\Delta^{S\text{-}RSRE} = \min\{n \geq 0: E_n(\|R_n - R_{n+1}\|_2) \leq S(R_T) \cdot (E_n(c_{n+1}) - c_n)\}. \tag{16}$$

F. Implementing the Stopping Rules

In the monitored reconstruction process on each stage n we acquire an additional projection (or several projections) and obtain a partial reconstruction result $R_n$. In order to apply the stopping rules constructed in the previous subsection, the following values need to be estimated:

1. The expected distance $E_n(\|R_n - R_{n+1}\|_2)$ between the current reconstruction result and the next one.

2. The expected value $E_n(c_{n+1})$ of the cost function on the next stage of the process.

3. For implementation of the stopping rule (15), the $L_2$-norm of the last reconstruction result $\|R_T\|_2$.

4. For implementation of the stopping rule (16), the value of the Radon invariant $S(R_T)$, which can be calculated by analyzing the obtained projections $x_1, x_2, \ldots, x_n$.

The conventional method of modelling of the next result is not applicable for the case of tomography (as the assumption of the next projection $x_{n+1}$ having the same value as one of the previously acquired will lead to the same reconstruction result), thus in order to estimate the expected distance $E_n(\|R_n - R_{n+1}\|_2)$ other methods should be used, such as methods of time series forecasting. In certain embodiments, the most basic estimation method was used where the target expected distance is assumed to be close to the distance between the two most recently obtained results:

$$E_n(\|R_n - R_{n+1}\|_2) \approx \|R_{n-1} - R_n\|_2. \tag{17}$$

The method of estimating the expected cost function on the next stage inevitably depends on the cost structure. In the performed experiments it was assumed the "anydose" algorithm model: each batch of acquired projections imparts a fixed dose c>0, the exposure between projections is negligible, the time required to perform reconstruction is disregarded, and the cost function is proportional to the number of acquired projections (7). In this model, the difference between the expected cost function value on the next process stage and the current cost function simply equals the constant c:

$$E_n(c_{n+1}) - c_n = c. \tag{18}$$

In order to implement the stopping rule (15) we assumed the following dependence model between the reconstruction result norm and the stage number n:

$$\|R_n\|_2 \approx \frac{a_0}{a_1 + n} + a_2. \tag{19}$$

The model parameters $a_0$, $a_1$, and $a_2$ of the regression (19) were determined at each stage n using the observed norms $\|R_1\|_2$, $\|R_2\|_2$, ..., $\|R_n\|_2$ of the available reconstruction results in the following way: a ternary search through the values of $a_1$ on the outer level was used, then with a fixed value of $a_1$ the values of $a_0$ and $a_2$ were determined using a simple linear least squares fitting. Using the found parameters on each stage we extrapolated the value of $\|R_T\|_2$.

Finally, to implement the stopping rule (16) the Radon invariant $S(R_T)$ needs to be estimated. Its value does not differ significantly from the values $S(R_1)$, $S(R_2)$, ..., $S(R_n)$ and from the sums of elements in each projection $S(x_1)$, $S(x_2)$, ..., $S(x_n)$. To reduce the noise, all currently available projections can be used to calculate:

$$S(R_T) \approx \frac{1}{n}\sum_{i=1}^{n} S(x_i). \quad (20)$$

With the established framework the hypotheses can be tested and the monitored tomographic reconstruction process can be evaluated.

II. EXPERIMENTAL EVALUATION

In this section the monitored reconstruction model evaluation on tomographic data obtained using laboratory microtomography setup in FSRC "Crystallography and photonics" of the Russian academy of sciences is presented. Subsection II-A provides information about the evaluated objects and their 2D sections, subsection II-B is dedicated to the evaluation of partial reconstruction errors and testing hypotheses H1 and H2, and subsection II-C contains the evaluation results for the implemented stopping rules.

A. Evaluated Objects

For experimental evaluation of the monitored tomographic reconstruction model described in Section I five 2D sections of different objects were used, obtained using the same laboratory X-ray tomography setup. Description of the evaluated objects, their sections, and published works related to the published imaging data, is presented in Table 1.

The sinograms are obtained using the same X-ray laboratory microtomography setup developed in FSRC "Crystallography and Photonics" RAS, with a high voltage source GE ISOVOLT 3003, X-ray tube with molybdenum anode and XIMEA-xiRay 11Mpix X-ray detector with pixel size 9 μm. There were no absorption filters between the X-ray source and the object. All tomographic projections of all samples were obtained with 20 mA current and 40 kV voltage setting. The experimental characteristics which differed between the objects are listed in Table 2.

TABLE 1

| Object code | Description |
| --- | --- |
| PG-CA | Human pineal gland, section with visible calcification |
| PG-EM | Human pineal gland, section without calcification |
| GB | Gerbil bone section |
| HT | Human tooth section with lead filling |
| PM | Polylactide matrix section |

TABLE 2

| Characteristic | PG-CA | PG-EM | GB | HT | PM |
| --- | --- | --- | --- | --- | --- |
| Emitter-object dist. | 1.3 m | 1.3 m | 1.2 m | 1.2 m | 1.2 m |
| Object-detector dist. | 0.02 m | 0.02 m | 0.05 m | 0.05 m | 0.05 m |
| Exposition | 10 s | 10 s | 5 s | 5 s | 2.5 s |
| Num. of projections | 400 | 400 | 400 | 400 | 2000 |
| Angular step | 0.5° | 0.5° | 0.5° | 0.5° | 0.1° |

Figure 3:
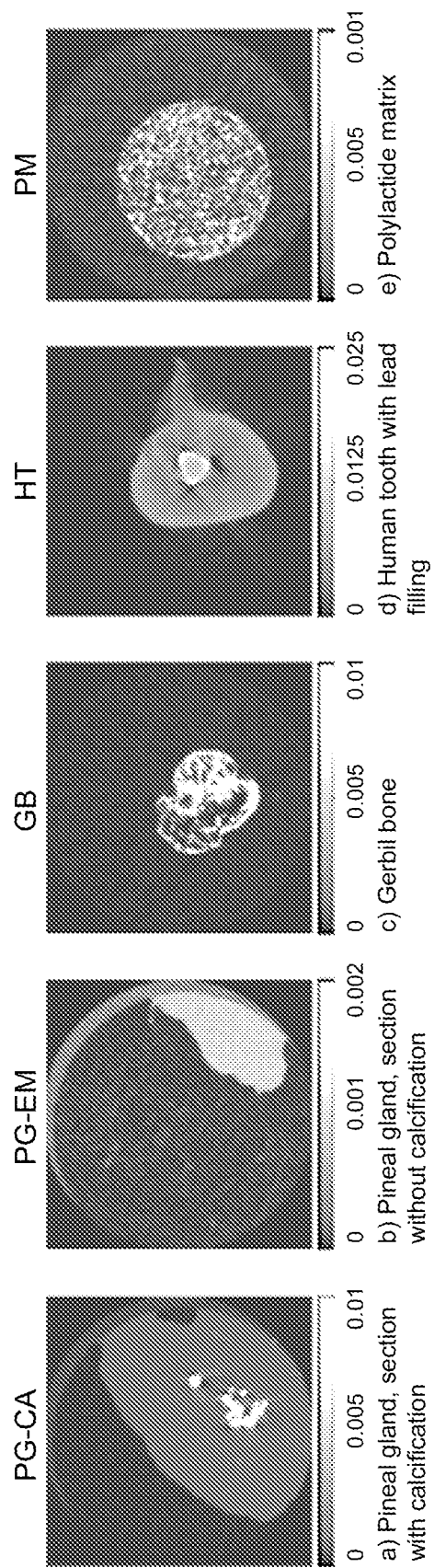
FIG. 3 provides images illustrating reconstructed images for evaluated 2D sections generated in the process of FIG. 2.

For all object sections, only the central square regions with size 1024×1024 px were evaluated. Reconstruction was performed using FBP method implemented in scikit image 0.16.2. Reconstructed images for the evaluated 2D sections are presented in FIG. 3.

B. Evaluating Partial Reconstructions

For each object 360 projections in the angular range [0°, 180°] with the angular step of 0.5° were selected, sampled at random without repetitions. The sequence of projections is constructed once for each evaluated object and is used in all further experiments with this object. Partial reconstructions were performed after adding five projections at a time from the sampled sequence. The random projection collection protocol allows to demonstrate the monitored reconstruction effects more clearly, while still remaining realistic. For example, such a sampling protocol could be supported with electron beam computed tomography (EBCT) set-ups.

Figure 4:
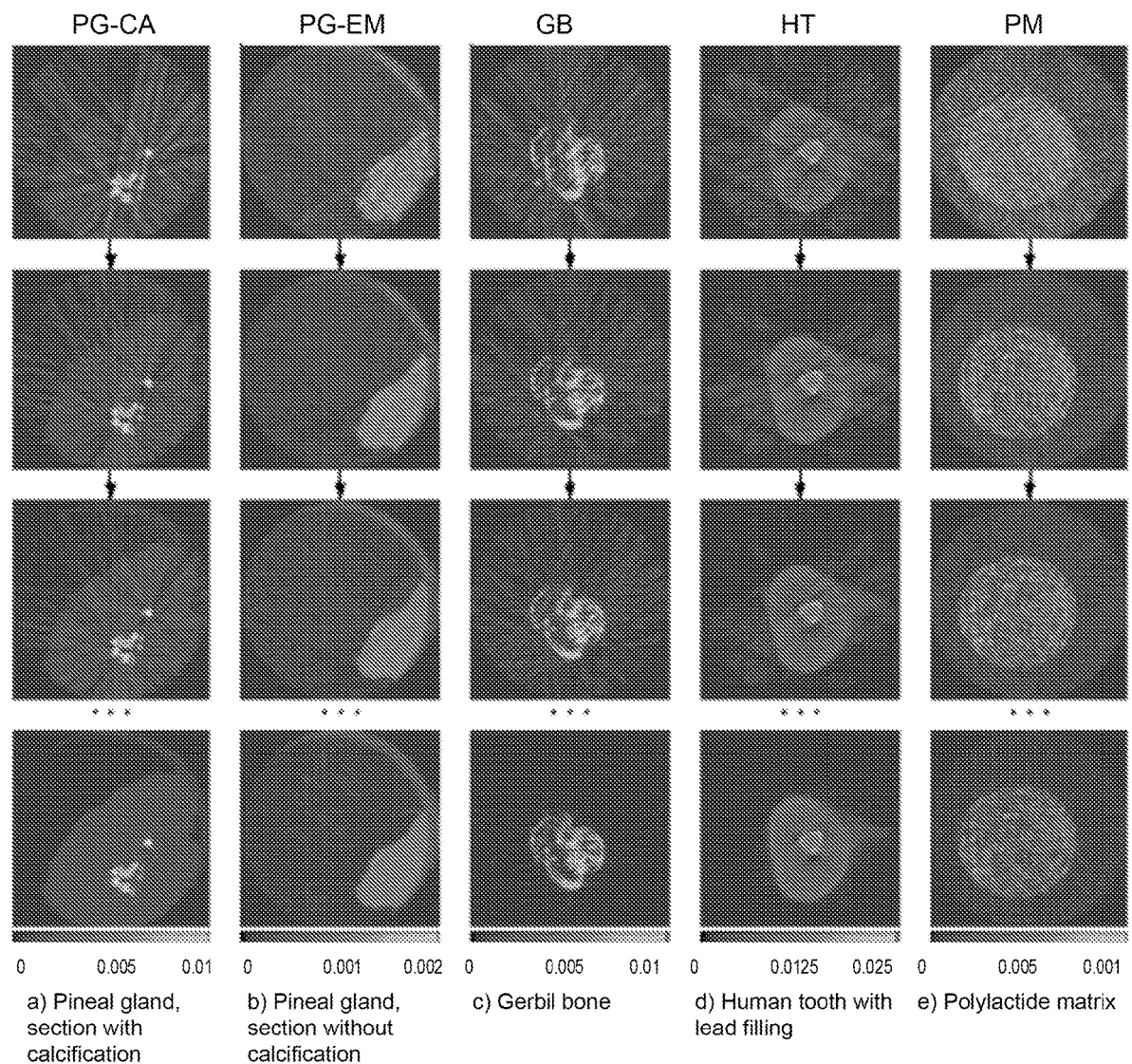
FIG. 4 provides images illustrating the partial reconstruction for the images illustrated in FIG. 3 performed using the FBP method.

After taking the next five projections the partial reconstruction was performed using the FBP method. Examples of partial reconstructions are presented in FIG. 4.

Figure 5A:
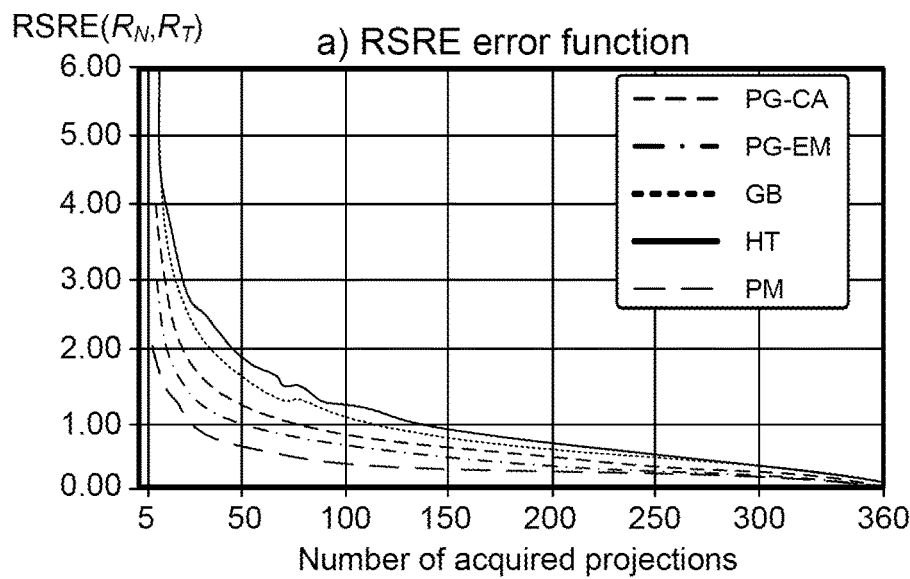
FIGS. 5A-C are graphs illustrating the convergence of the partial reconstruction results to the last reconstruction result $R_T$ if the functions RSRE (8), NRSRE (9), and S-RSRE (10) are used to represent the error function $\varepsilon(R_n, \theta)$.
Figure 5B:
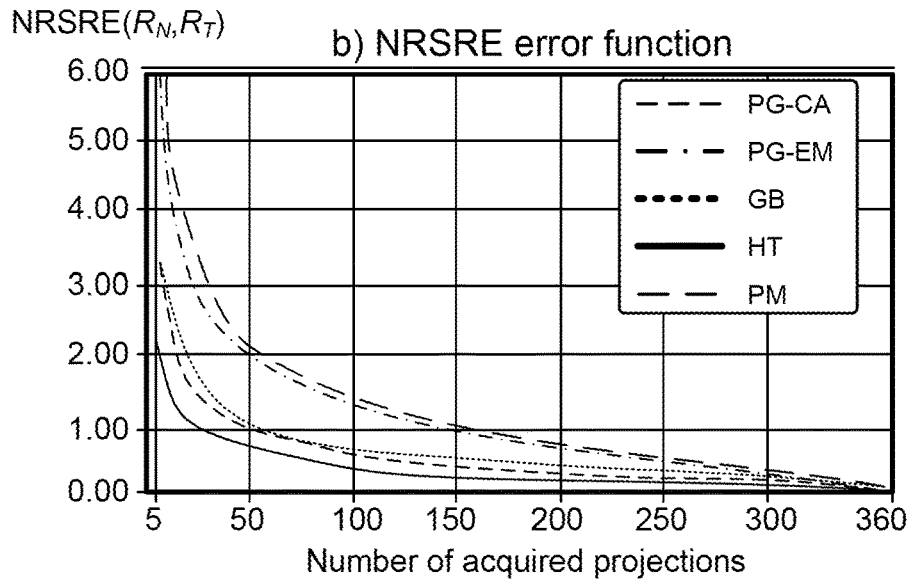
Figure 5C:
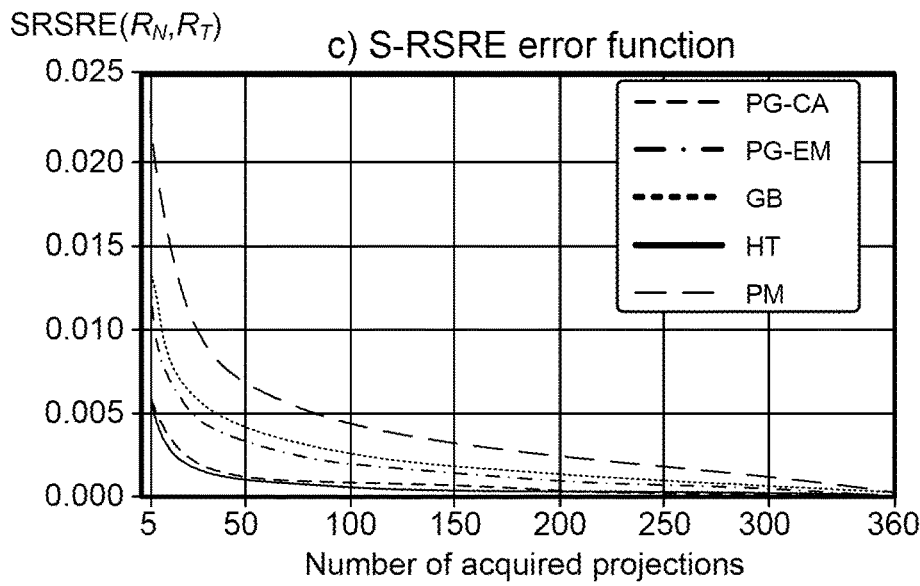

FIG. 5 illustrates the convergence of the partial reconstruction results to the last reconstruction result $R_T$ if the functions RSRE (8), NRSRE (9), and S-RSRE (10) are used to represent the error function $\varepsilon(R_n, \theta)$. It is clear that for each error function the convergence speed is different for different objects, the grouping of the objects by the convergence speed is different for each error function, and no grouping corresponds to the specific experimental characteristics presented in Table 2. This data supports the hypothesis H1, that the decrease speed of the error depends on the object, at least for the error functions evaluated herein. Error function values for the partial reconstruction results, corresponding to the plots in FIGS. 5A-C are presented in Table 3.

TABLE 3

| Object | RSRE (8) | | | | NRSRE (9) | | | | S-RSRE (10) | | | |
| --- | --- | --- | --- | --- | --- | --- | --- | --- | --- | --- | --- | --- |
| code | 50 ang. | 150 ang. | 250 ang. | 350 ang. | 50 ang. | 150 ang. | 250 ang. | 350 ang. | 50 ang. | 150 ang. | 250 ang. | 350 ang. |
| PG-CA | 1.1240 | 0.5309 | 0.3023 | 0.0807 | 0.9175 | 0.4334 | 0.2468 | 0.0658 | 0.0017 | 0.0008 | 0.0005 | 0.0001 |
| PG-EM | 0.8594 | 0.4094 | 0.2287 | 0.0580 | 1.8198 | 0.8669 | 0.4844 | 0.1229 | 0.0035 | 0.0017 | 0.0009 | 0.0002 |

TABLE 3-continued

| Object | RSRE (8) | | | | NRSRE (9) | | | | S-RSRE (10) | | | |
|---|---|---|---|---|---|---|---|---|---|---|---|---|
| code | 50 ang. | 150 ang. | 250 ang. | 350 ang. | 50 ang. | 150 ang. | 250 ang. | 350 ang. | 50 ang. | 150 ang. | 250 ang. | 350 ang. |
| GB | 1.5421 | 0.7257 | 0.4168 | 0.1101 | 0.9922 | 0.4670 | 0.2682 | 0.0709 | 0.0040 | 0.0019 | 0.0011 | 0.0003 |
| HT | 1.7632 | 0.8143 | 0.4529 | 0.1178 | 0.6263 | 0.2892 | 0.1609 | 0.0419 | 0.0015 | 0.0007 | 0.0004 | 0.0001 |
| PM | 0.5955 | 0.2858 | 0.1609 | 0.0405 | 2.0225 | 0.9705 | 0.5463 | 0.1375 | 0.0070 | 0.0034 | 0.0019 | 0.0005 |

To check the hypothesis H2, which is necessary to apply the stopping rules (14), (15), and (16), derived in subsection I-E, the $L_2$-distances between consecutive partial reconstruction results decrease as the number of acquired projections increases. The plotted distances between the consecutive reconstruction results for all objects are presented in FIG. 6, the corresponding distance values are presented in Table 4. A general decreasing trend in support of the hypothesis H2 can be observed, although some discrepancies are present for object "HT", mostly when fewer projection angles are considered.

TABLE 4

| | 50 | 100 | 150 | 200 | 250 | 300 | 350 |
|---|---|---|---|---|---|---|---|
| PG-CA | 0.3689 | 0.1864 | 0.1282 | 0.0922 | 0.0785 | 0.0618 | 0.0602 |
| PG-EM | 0.3039 | 0.1454 | 0.0954 | 0.0719 | 0.0574 | 0.0473 | 0.0412 |
| GB | 0.4897 | 0.2552 | 0.1674 | 0.1427 | 0.1028 | 0.0895 | 0.0778 |
| HT | 0.6188 | 0.2864 | 0.1953 | 0.1448 | 0.1095 | 0.0944 | 0.0815 |
| PM | 0.1954 | 0.1000 | 0.0665 | 0.0510 | 0.0404 | 0.0340 | 0.0287 |

After the preliminary examination of the partial reconstruction results is performed, of the constructed stopping rules can be evaluated.

C. Evaluating the Stopping Rules

The application of the stopping rules to the process of monitored tomographic reconstruction should allow achieving lower mean error level given a fixed mean number of acquired projections, or, respectively, the lower mean number of projections for the same mean error level. In order to evaluate and visualize that, it is convenient to analyze the expected performance profiles of the stopping rules.

Such performance profiles are obtained by plotting the mean error level (in this case it is expressed in terms of the error function $\varepsilon(R_n, \theta)$ value averaged throughout the analyzed objects) of the partial reconstruction results against the mean number of projections acquired before the stopping condition is met, while varying the cost parameter c.

To provide a reference, in the same axes we can plot the mean error level achieved by reconstructing the objects with a fixed number of acquired projections. Such performance profile gives a baseline stopping method—the one which always stops at a fixed stage, i.e. after a fixed predefined number of projections are acquired.

Figure 7A:
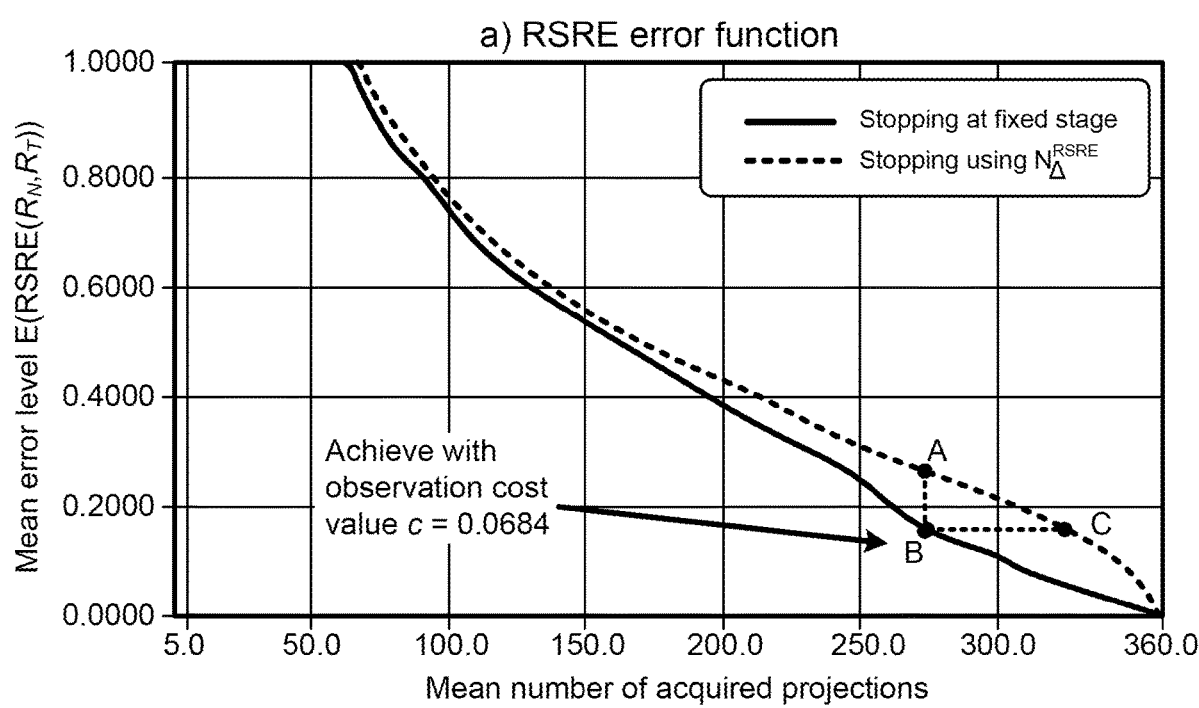
FIGS. 7A-C are graphs illustrating the expected performance profiles of constructed stopping rules for reconstruction, alongside the baseline methods which stops at a fixed stage, using the RSRE, NRSRE, and S-RSRE metrics, respectively.
Figure 7B:
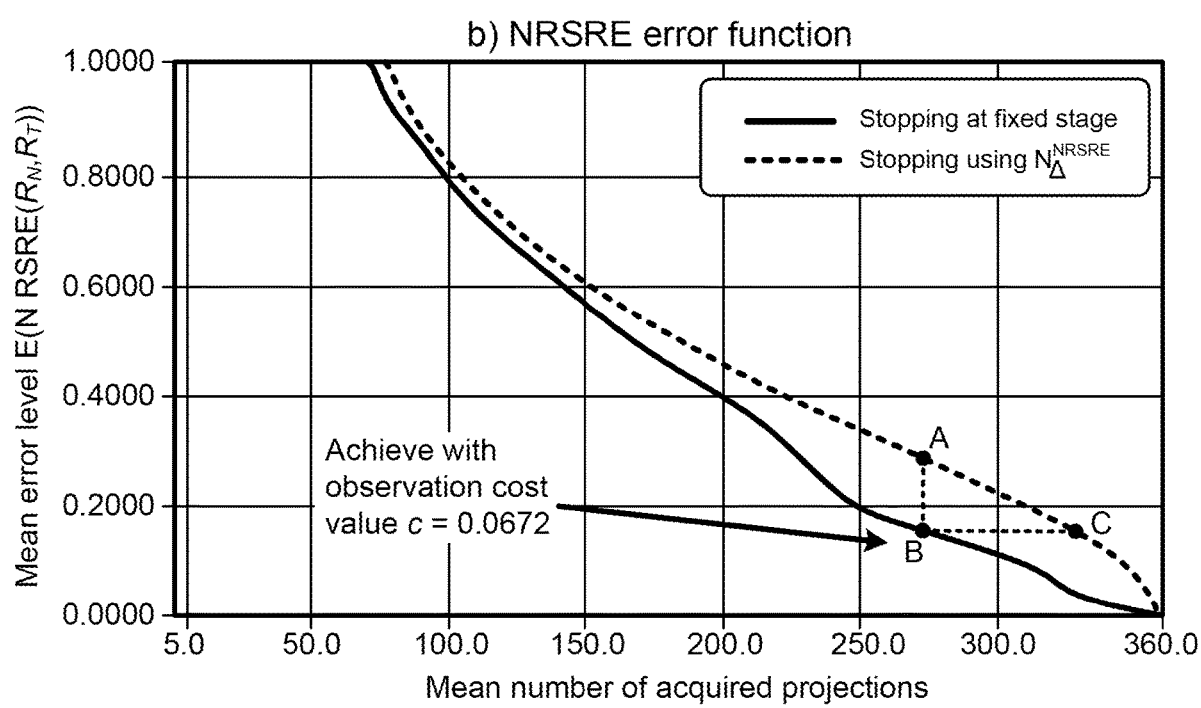
Figure 7C:
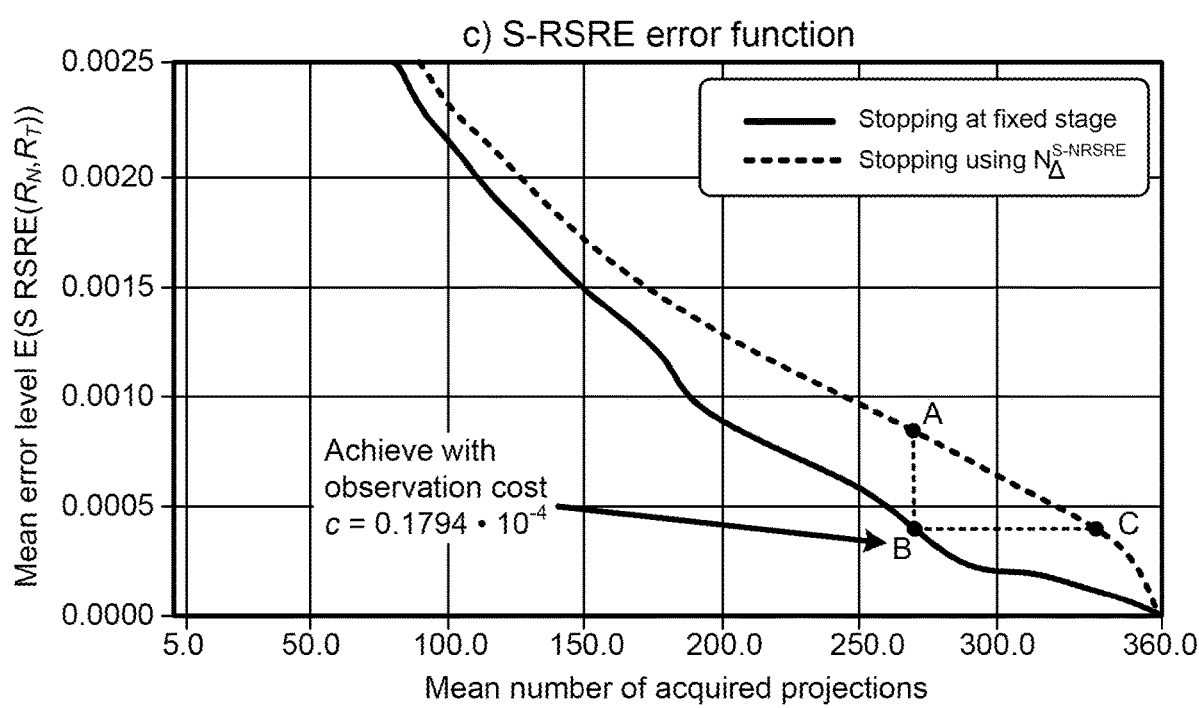

The expected performance profiles of the constructed stopping rules, alongside the baseline methods which stops at a fixed stage, are presented in FIGS. 7A-C. Each point of the baseline plots is obtained by fixing the number of acquired projections and calculating the mean error function value for the reconstruction results of all objects. Each point of the stopping rule performance profile is obtained in a different way: with a fixed value of the observation cost c the monitored reconstruction was performed for each object, and the coordinates of the point were calculated by taking the mean number of acquired projections (averaged throughout the analyzed objects), and the corresponding mean error level achieved at stopping time.

Consider points A, B, and C on FIG. 7A (corresponding to the experiment with RSRE error function (8)). Point A corresponds to the mean RSRE error level of 0.2627 which is achieved if for all objects we acquired and processed exactly 275 projection angles. Point B corresponds to the monitored reconstruction with the stopping rule (14) and observation cost value c=0.0684. According to this stopping rule, the process stopped at different stages for different objects—namely, it stopped after 285 projections for the object "PG-CA", after 220 projections for "PG-EM", after 155 projections for the object "PM", and it never stopped for the objects "GB" and "HT" (which is to say that it stopped after 360 projections were obtained). As a result, the mean RSRE error level amounted to 0.1583. If all objects were to stop at the same stage, 325 projections had to be processed in order to achieve the same mean error level—on the baseline plot it corresponds to point C.

The coordinates of points A, B, and C presented on each subplot of FIGS. 7A-C along with the number of acquired projections and the reconstruction error level at stopping time for each object are presented in Tables 5A-C.

It is evident that the performance profiles for the constructed stopping rules are positioned below the profiles of the baseline method for all evaluated error functions, which means that by making the stopping decision with monitored reconstruction allows to achieve lower mean error levels with the same mean number of acquired projections (i.e. the same mean imparted dose) and, conversely, allows to obtain the reconstruction result with the same mean error level by taking fewer projections on average.

Table 6 shows the achieved mean error level (in terms of the evaluated error functions) at stopping time, using the constructed stopping methods, and with a restriction to the mean number of acquired projections, which corresponds to a restricted mean dose. The mean error values presented in Tables 6A-C correspond to points of the stopping method's performance profile which yield the closest mean number of acquired projections without exceeding the limitation. It can be observed, that the application of the stopping rule allows lower mean reconstruction error levels to be achieved, than the baseline for each evaluated error function and for each restriction level.

TABLE 5A a) RSRE (8) error function and $N_A^{RSRE}$ (14) stopping rule

| Object code | Point A | | Point B | | Point C | |
|---|---|---|---|---|---|---|
| | Angles | Error | Angles | Error | Angles | Error |
| PG-CA | 275 | 0.2556 | 285 | 0.2382 | 325 | 0.1534 |
| PG-EM | 275 | 0.1909 | 220 | 0.2757 | 325 | 0.1120 |
| GB | 275 | 0.3416 | 360 | 0.0000 | 325 | 0.1984 |
| HT | 275 | 0.3911 | 360 | 0.0000 | 325 | 0.2418 |
| PM | 275 | 0.1342 | 155 | 0.2778 | 325 | 0.0794 |
| Mean | 275 | 0.2627 | 276 | 0.1583 | 325 | 0.1570 |

TABLE 5B b) NRSRE (9) error function and $N_A^{NRSRE}$ (15) stopping rule

| Object code | Point A | | Point B | | Point C | |
|---|---|---|---|---|---|---|
| | Angles | Error | Angles | Error | Angles | Error |
| PG-CA | 275 | 0.2086 | 245 | 0.2530 | 330 | 0.1176 |
| PG-EM | 275 | 0.4042 | 360 | 0.0000 | 330 | 0.2185 |
| GB | 275 | 0.2198 | 245 | 0.2723 | 330 | 0.1182 |
| HT | 275 | 0.1389 | 160 | 0.2782 | 330 | 0.0757 |
| PM | 275 | 0.4558 | 360 | 0.0000 | 330 | 0.2472 |
| Mean | 275 | 0.2855 | 274 | 0.1607 | 330 | 0.1554 |

TABLE 5C c) S-RSRE (10) error function and $N_A^{S-RSRE}$ (16) stopping rule
Error levels are multiplied by 1,000

| Object code | Point A | | Point B | | Point C | |
|---|---|---|---|---|---|---|
| | Angles | Error | Angles | Error | Angles | Error |
| PG-CA | 270 | 0.3939 | 160 | 0.7624 | 335 | 0.1912 |
| PG-EM | 270 | 0.8170 | 335 | 0.3851 | 335 | 0.3851 |
| GB | 270 | 0.9545 | 360 | 0.0000 | 335 | 0.4477 |
| HT | 270 | 0.3383 | 135 | 0.7507 | 335 | 0.1586 |
| PM | 270 | 1.6543 | 360 | 0.0000 | 335 | 0.7794 |
| Mean | 270 | 0.8316 | 270 | 0.3796 | 335 | 0.3924 |

TABLE 6A a) RSRE (8) error function and $N^{S-RSRE}_\Delta$ (15) stopping rule

| Stopping method | Limitation to the mean number of projection angles | | | | | | |
|---|---|---|---|---|---|---|---|
| | ≤50 | ≤100 | ≤150 | ≤200 | ≤250 | ≤300 | ≤350 |
| Baseline | 1.177 | 0.771 | 0.553 | 0.421 | 0.312 | 0.211 | 0.081 |
| $N^{S-RSRE}_\Delta$ | 1.153 | 0.739 | 0.544 | 0.399 | 0.259 | 0.128 | 0.024 |

TABLE 6B b) RSRE (9) error function and $N^{S-RSRE}_\Delta$ (14) stopping rule

| Stopping method | Limitation to the mean number of projection angles | | | | | | |
|---|---|---|---|---|---|---|---|
| | ≤50 | ≤100 | ≤150 | ≤200 | ≤250 | ≤300 | ≤350 |
| Baseline | 1.276 | 0.832 | 0.605 | 0.458 | 0.341 | 0.229 | 0.088 |
| $N^{S-RSRE}_\Delta$ | 1.228 | 0.797 | 0.582 | 0.449 | 0.206 | 0.138 | 0.025 |

TABLE 6C c) RSRE (10) error function and $N^{S-RSRE}_\Delta$ (16) stopping rule
Error levels are multiplied by 1000

| Stopping method | Limitation to the mean number of projection angles | | | | | | |
|---|---|---|---|---|---|---|---|
| | ≤50 | ≤100 | ≤150 | ≤200 | ≤250 | ≤300 | ≤350 |
| Baseline | 3.543 | 2.309 | 1.684 | 1.276 | 0.951 | 0.635 | 0.244 |
| $N^{S-RSRE}_\Delta$ | 3.367 | 2.162 | 1.504 | 0.893 | 0.595 | 0.226 | 0.087 |

Figure 8:
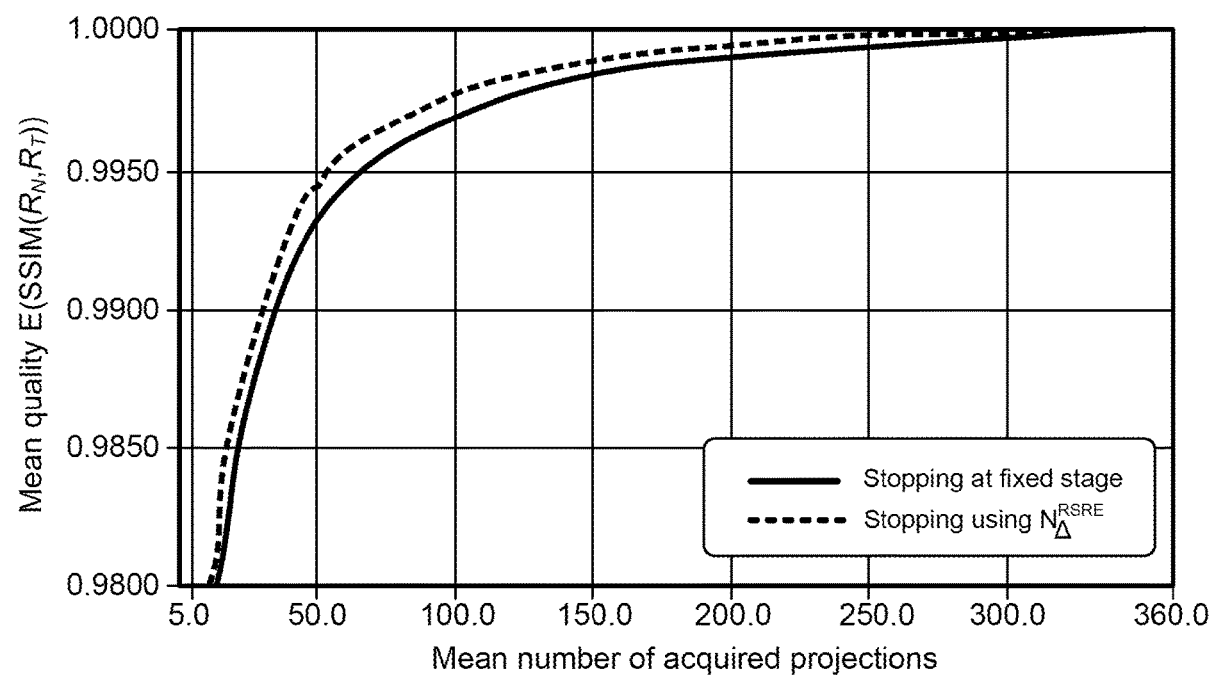
FIG. 8 is a graph illustrating the expected performance profiles of a constructed stopping rule for reconstruction, alongside the baseline method which stops at a fixed stage, using the SSIM quality metric.

The selection of the error function for the reconstruction result may depend significantly on the practical application and setup. As it was shown in subsection I-E, the construction of the stopping rule requires for the structure of the error function to be known, and if other quality metrics are used, the appropriate stopping rules should be specifically constructed for them; however, for some quality metrics, the stopping rules can provide good results without modification. For example, if the structural similarity metric SSIM is used, the stopping rule (14) outperforms stopping at a fixed stage (see FIG. 8 and Table 7), presumably due to a correlation between SSIM and RSRE (8) on the analyzed dataset. For calculation of SSIM metric we used its implementation in scikit-image 0.16.2 with default parameters and data range length of 1.0 for reconstructed images with floating-point data type.

TABLE 7

| Stopping method | Limitation to the mean number of projections | | | | | | |
|---|---|---|---|---|---|---|---|
| | ≤50 | ≤100 | ≤150 | ≤200 | ≤250 | ≤300 | ≤350 |
| Baseline | 0.9929 | 0.9968 | 0.9984 | 0.9991 | 0.9995 | 0.9998 | 1.0000 |
| $N_A^{RSRE}$ | 0.9944 | 0.9977 | 0.9988 | 0.9994 | 0.9998 | 0.9999 | 1.0000 |

V. CONCLUSION

For the evaluation of a monitored reconstruction process in an "anydose" model, five sinograms of object sections were used, collected with the laboratory X-ray tomography set-up in a parallel scheme. Partial reconstructions were performed in stages, where on each stage five new random projections were drawn from the sinogram to update the reconstructed image. FIGS. 5A-C illustrate the dynamics of the error level, calculated in three different ways, with regards to the process stage. Since the main experimental parameters (projections collection protocol, tube current, anode type, detector, etc.) were the same, the differences in the error level curves signify the dependence of the dynamic error behavior on inherent properties of the probed object.

It is worth to note that the ordering of plots in FIG. 5 by the speed of the error decrease given a fixed experimental setup and error function is interesting in itself, as it suggests a method of objects classification by some inherent properties.

Figure 6:
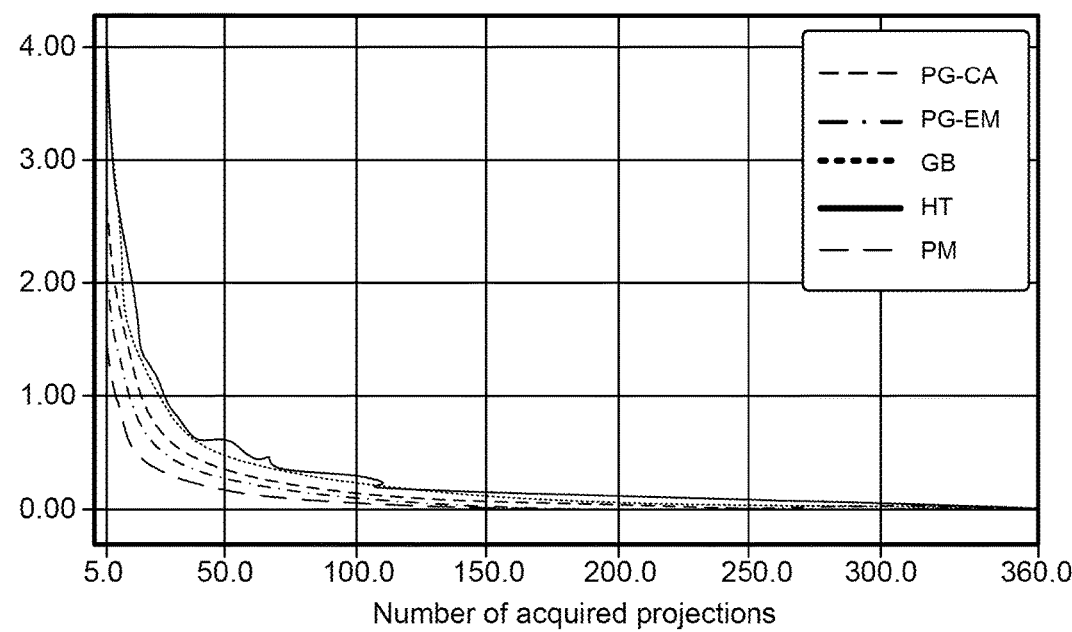
FIG. 6 is a diagram illustrating the plotted distances between the consecutive reconstruction results for all objects presented in the images of FIG. 3.

FIG. 6 shows the decrease of $L_2$-distances between consecutive partial reconstruction results from stage to stage. This decrease (referred to in the hypothesis H2) is required in order for the constructed stopping rules to be consistent: since these distances are thresholded in the stopping rules, their decrease guarantees that if the stopping condition is met, it will be met at the future stages as well (and thus it is reasonable to stop at the current stage). Deviations from the decreasing trend will impact the stopping rules as follows: minor discrepancies, which lead to the observed distance being higher than expected, such as the ones seen for the object "HT" in FIG. 6, may lead to a delayed stopping; however, if the measured distance will deviate in the other direction (i.e. will be lower than expected), it could lead to preliminary stopping before the desired reconstruction quality is reached. This could be mitigated by increasing the number of projections added at each stage of the process.

FIG. 7 illustrates the averaged experimental profiles of two types: reconstruction with stopping at a fixed stage (that is, after a fixed given number of projections is collected), and with stopping using the constructed stopping rules (14)-(16). The presented results confirm that the monitored reconstruction approach in an "anydose" model allows to reduce the mean reconstruction error with a given mean number of analyzed projections.

The experiments in Section III were conducted on 2D sections; however, the monitored reconstruction framework presented in Section I is applicable for a full 3D reconstruction as well. Moreover, even the results in 2D could be relevant for practical applications, as it might be feasible to make a stopping decision for 3D reconstruction by analyzing partial reconstructions of one or several central sections.

One of the limitations of the monitored reconstruction approach is the dependence on the protocol for acquiring projections, as it is required for the partial reconstructions to produce meaningful results, improving over time according to a selected metric function. The random projections sampling evaluated in Section II conforms to this requirement, but may constrain the practical implementation.

A major disadvantage of the monitored reconstruction process is the need to perform partial reconstructions in order to estimate the change of the error level on the next stage and implement the stopping rule. For an "anydose" model the extra computational cost associated with partial reconstructions is less relevant, as the main target of such model is the reduction of the number of X-ray projections, however it is relevant if scanning time or reconstruction time is an important factor contributing to the observation cost function (1). While for integral reconstruction methods such as FBP the partial reconstructions can be updated after obtaining new projection angles, in order to achieve the same for the iterative methods, some special techniques should be designed and implemented.

VI. COMPUTER ENVIRONMENT

Figure 9:
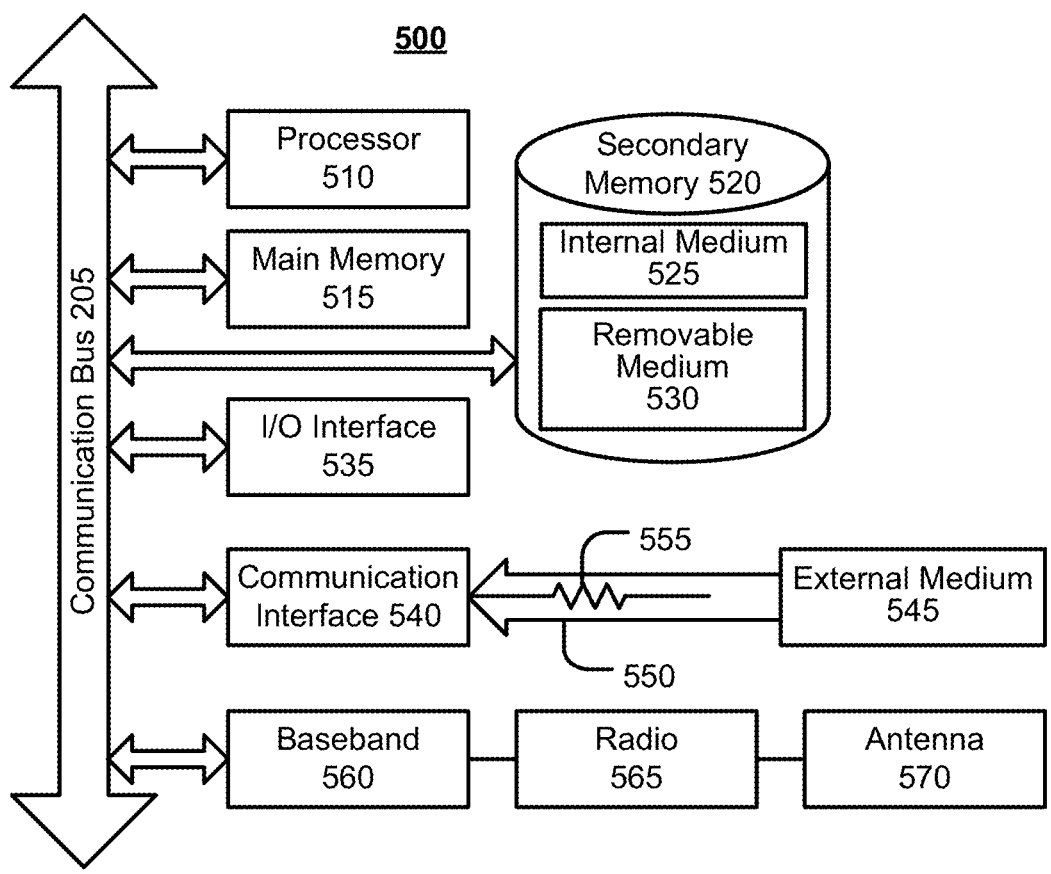
FIG. 9 is a block diagram illustrating an example wired or wireless system that can be used in connection with various embodiments described herein.

FIG. 9 is a block diagram illustrating an example wired or wireless system 550 that can be used in connection with various embodiments described herein. For example the system 550 can be used as or in conjunction with or to implement the processes described above, and may represent components of backend server(s), and/or other devices used to perform the processes described. The system 550 can be a server or any conventional personal computer, or any other processor-enabled device that is capable of wired or wireless data communication. Other computer systems and/or architectures may be also used, as will be clear to those skilled in the art.

Figure 2:
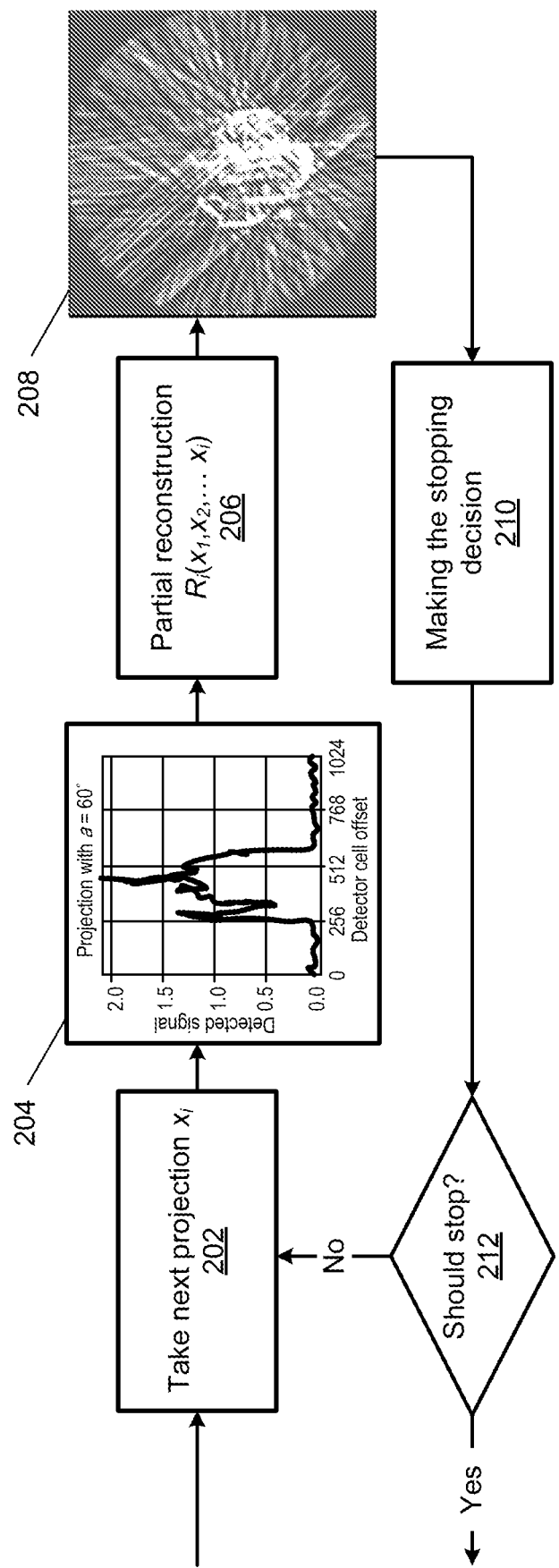
FIG. 2 is a diagram illustrating an example of the full model of a monitored tomographic reconstruction process in accordance with another example embodiment.

Thus, such a server can comprise at least one hardware processor; and one or more software modules that, when executed by the at least one hardware processor perform the processes described above, i.e., the process of receiving the projections, generating eth partial reconstructions and making the stopping decision as illustrated in FIG. 2. The projections can be received from the scanner via I/O interface 535 or possibly, communication interface 540, or even the radio 565, which are described in more detail below.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., backend processor), an additional microprocessor or controller for dual or multiple processor systems, or a coprocessor. Such auxiliary processors may be discrete processors or may be integrated with the processor 560. Examples of processors which may be used with system 550 include, without limitation, the Pentium® processor, Core i7@ processor, and Xeon® processor, all of which are available from Intel Corporation of Santa Clara, Calif.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

System 550 preferably includes a main memory 565 and may also include a secondary memory 570. The main memory 565 provides storage of instructions and data for programs executing on the processor 560, such as one or more of the functions and/or modules discussed above. It should be understood that programs stored in the memory and executed by processor 560 may be written and/or compiled according to any suitable language, including without limitation C/C++, Java, JavaScript, Pearl, Visual Basic, NET, and the like. The main memory 565 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

The secondary memory 570 may optionally include an internal memory 575 and/or a removable medium 580, for example a floppy disk drive, a magnetic tape drive, a compact disc (CD) drive, a digital versatile disc (DVD) drive, other optical drive, a flash memory drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer-readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 590. Examples of external storage medium 595 may include an external hard disk drive or an external optical drive, or and external magneto-optical drive.

Other examples of secondary memory 570 may include semiconductor-based memory such as programmable read-only memory (PROM), erasable programmable read-only memory (EPROM), electrically erasable read-only memory (EEPROM), or flash memory (block oriented memory similar to EEPROM). Also included are any other removable storage media 580 and communication interface 590, which allow software and data to be transferred from an external medium 595 to the system 550.

System 550 may include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 550 with a network or another computing device.

Communication interface 590 preferably implements industry promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

In an embodiment, I/O interface 585 provides an interface between one or more components of system 550 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

The system 550 also includes optional wireless communication components that facilitate wireless communication over a voice and over a data network. The wireless communication components comprise an antenna system 610, a radio system 615 and a baseband system 620. In the system 550, radio frequency (RF) signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown).

Various embodiments may also be implemented primarily in hardware using, for example, components such as application specific integrated circuits (ASICs), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application.

While certain embodiments have been described above, it will be understood that the embodiments described are by way of example only. Accordingly, the systems and methods described herein should not be limited based on the described embodiments. Rather, the systems and methods described herein should only be limited in light of the claims that follow when taken in conjunction with the above description and accompanying drawings.

What is claimed is:

1. A system for monitored tomographic reconstruction, comprising:
   at least one hardware processor; and
   one or more software modules that, when executed by the at least one hardware processor, over one or more stages,
      receive a plurality of projections from detectors, configured to capture a plurality of projections for each scan of an x-ray generator configured to generate x-ray beams for scanning an object, and as the plurality of projections is received, generate a partial reconstruction result, and make a stopping decision with respect to whether or not another projection should be obtained based on a stopping problem that defines when a reconstructed image quality of the partial reconstruction result is sufficient with respect to the expended cost as determined by a stopping rule.

2. The system of claim 1, wherein a system loss function at a stage n is defined as a sum of a reconstruction error and a cost function, depending on the plurality of projections obtained up to stage n.

3. The system of claim 1, wherein reconstruction to generate the partial reconstruction result uses an integral reconstruction technique.

4. The system of claim 3, wherein the integral reconstruction technique uses Filtered Back Projection (FBP).

5. The system of claim 1, wherein reconstruction to generate the partial reconstruction result uses an iterative algebraic reconstruction technique.

6. The system of claim 1, and wherein the stopping problem uses the following cost function:

$$c_n(x_1, \ldots, x_n) = n \cdot c,$$

wherein c is an observation cost, n is a current one of the one or more stages, and x is one of the plurality of projections.

7. The system of claim 1, wherein the stopping problem uses at least one of the following reconstruction error functions:

$$RSRE(R_n, \theta) = \|R_n - R*(\theta)\|_2,$$

$$NRSRE(R_n, \theta) = \frac{\|R_n - R*(\theta)\|_2}{\|R*(\theta)\|_2},$$

$$S\text{-}RSRE(R_n, \theta) = \frac{\|R_n - R*(\theta)\|_2}{S(R*(\theta))},$$

$$NRSRE(R_n, \theta) = \frac{\|R_n - R*(\theta)\|_2}{\|R*(\theta)\|_2}; \text{ and}$$

$$S\text{-}RSRE(R_n, \theta) = \frac{\|R_n - R*(\theta)\|_2}{S(R*(\theta))},$$

wherein $R_n$ is a partial reconstruction result at stage n of the one or more stages $R*(\theta)$ represents an ideal image of the object, and $S(R*(\theta))$ is a sum of pixel values of the ideal image of the object.

8. The system of claim 1, wherein the stopping rule is at least one of the following:

$$N_\Delta^{RSRE} = \min\{n \geq 0 : E_n(\|R_n - R_{n+1}\|_2) \leq \leq E_n(c_{n+1}) - c_n\},$$

$$N_\Delta^{NRSRE} = \min\{n \geq 0 : E_n(\|R_n - R_{n+1}\|_2) \leq \leq \|R_T\|_2 \cdot (E_n(c_{n+1}) - c_n)\}$$

$$N_\Delta^{S\text{-}RSRE} = \min\{n \geq 0 : E_n(\|R_n - R_{n+1}\|_2) \leq \leq S(R_T) \cdot (E_n(c_{n+1}) - c_n)\},$$

$$N_\Delta^{RSRE} = \min\{n \geq 0 : E_n(\|R_n - R_{n+1}\|_2) \leq \leq E_n(c_{n+1}) - c_n)\},$$

$$N_\Delta^{RSRE} = \min\{n \geq 0 : E_n(\|R_n - R_{n+1}\|_2) \leq \leq \|R_T\|_2 \cdot (E_n(c_{n+1}) - c_n)\}, \text{ and}$$

$$N_\Delta^{RSRE} = \min\{n \geq 0 : E_n(\|R_n - R_{n+1}\|_2) \leq \leq S(R_T) \cdot (E_n(c_{n+1}) - c_n)\}.$$

wherein n is a current stage of the one or more stages, $R_n$ is a partial reconstruction result at stage n, $R_T$ is a full reconstruction result, $S(R_T)$ is a Radon invariant of the full reconstruction result at a last stage, $E_n$ denotes a conditional expected value at stage n after n observations have been made, and $c_n$ is a cost function at stage n.

9. The system of claim 1, wherein making the stopping decision comprises:
estimating the expected distance between a current reconstruction result and a next reconstruction result,
an expected value of a cost function related to obtaining another projection, and
thresholding the estimated expected distance for making the stopping decision.

10. The system of claim 9, wherein making the stopping decision further comprises estimating an $L_2$-norm of a last full reconstruction result.

11. The system of claim 9, wherein making the stopping decision further comprises estimating a value of the Radon invariant $S(R_T)$.

12. The system of claim 1, wherein the partial reconstruction result is generated each time one of the plurality of projections is received.

13. The system of claim 1, wherein the partial reconstruction result is generated each time a predetermined number of the plurality of projections are received.

14. The system of claim 13, wherein the partial reconstruction result is generated each time five of the plurality of projections are received.

* * * * *